United States Patent
Kobayashi et al.

(10) Patent No.: US 11,226,334 B2
(45) Date of Patent: Jan. 18, 2022

(54) METHOD, BIOMARKER AND DIAGNOSTIC AGENT FOR DETECTION OF HIGH-RISK PROSTATE CANCER

(71) Applicants: J-OIL MILLS, INC., Tokyo (JP); OSAKA UNIVERSITY, Osaka (JP)

(72) Inventors: Yuka Kobayashi, Tokyo (JP); Kazutoshi Fujita, Osaka (JP); Norio Nonomura, Osaka (JP); Eiji Miyoshi, Osaka (JP)

(73) Assignees: J-CHEMICAL, INC., Tokyo (JP); OSAKA UNIVERSITY, Osaka (JP)

( * ) Notice: Subject to any disclaimer, the term of this patent is extended or adjusted under 35 U.S.C. 154(b) by 419 days.

(21) Appl. No.: 16/073,217

(22) PCT Filed: Feb. 3, 2017

(86) PCT No.: PCT/JP2017/003982
§ 371 (c)(1),
(2) Date: Jul. 26, 2018

(87) PCT Pub. No.: WO2017/138457
PCT Pub. Date: Aug. 17, 2017

(65) Prior Publication Data
US 2019/0049451 A1 Feb. 14, 2019

(30) Foreign Application Priority Data

Feb. 9, 2016 (JP) .............................. JP2016-022325

(51) Int. Cl.
*G01N 33/493* (2006.01)
*G01N 33/574* (2006.01)

(52) U.S. Cl.
CPC ..... *G01N 33/57434* (2013.01); *G01N 33/493* (2013.01); *G01N 2333/4724* (2013.01); *G01N 2333/96433* (2013.01); *G01N 2333/96455* (2013.01)

(58) Field of Classification Search
CPC .................................................. G01N 33/493
USPC .................................................... 424/130.1
See application file for complete search history.

(56) References Cited

U.S. PATENT DOCUMENTS

| | | | |
|---|---|---|---|
| 2011/0129849 A1* | 6/2011 | Zhang | G01N 33/57434 435/7.1 |
| 2011/0129938 A1 | 6/2011 | Kobayashi | |
| 2012/0282612 A1 | 11/2012 | Yamashita | |

FOREIGN PATENT DOCUMENTS

| | | |
|---|---|---|
| EP | 2395357 A1 | 12/2011 |
| JP | 4514163 B2 | 7/2010 |
| JP | 2011148735 A2 | 8/2011 |
| JP | 2011148736 A2 | 8/2011 |
| WO | 2010090264 A1 | 8/2010 |

OTHER PUBLICATIONS

Janković et al (Clinical Biochemistry, 2005, 38: 58-65).*
Hirabayashi et al (Chem Soc Rev, 2013, 42: 4443-4458).*
Kondo et al (Clinica Chimica Acta, 1995, 243: 1-9).*
International Search Report (ISR) dated Mar. 28, 2017 filed in PCT/JP2017/003982.
M. Tajiri et al., "Oligosaccharide profiles of the prostate specific antigen in free and complexed forms from the prostate cancer patient serum and in seminal plasma: a glycopeptide approach", Glycobiology vol. 18, No. 1, 2008, pp. 2-8.; Cited in Specification.
Miriam V. Dwek et al., "A sensitive assay to measure biomarker glycosylation demonstrates increased fucosylation of prostate specific antigen (PSA) in patients with prostate cancer compared with benign prostatic hyperplasia", Clinica Chimica Acta, 411, (2010), pp. 1935-1939.; Cited in Specification.
Yuka Kobayashi et al., "A Novel Core Fucose-specific Lectin from the Mushroom Pholiota squarrosa", J.Biol Chem, 2012, 287, pp. 33973-33982.; Cited in Specification.
Li, Q.K. et al., Serum Fucosylated Prostate-specific Antigen (PSA) Improves the Differentiation of Aggressive from Non-aggressive Prostate Cancers, Theranostics, Jan. 1, 2015, vol. 5, Issue 3, pp. 267-276.; Cited in ISR.

* cited by examiner

*Primary Examiner* — Sean E Aeder
(74) *Attorney, Agent, or Firm* — Rankin, Hill & Clark LLP

(57) ABSTRACT

[Problem] To provide a method for detecting high-risk prostate cancer, for the purpose of providing useful information, such as necessity of biopsy, to a test-positive patient in a PSA test.
[Solution] The method for detecting high-risk prostate cancer according to the present invention comprises reacting a PSA contained in a sample composed of urine collected from a human body which is suspected to be suffering from prostate cancer with (1) a fucose α1→6 affinitive lectin which has a characteristic property that the lectin has affinity expressed by a binding constant of $1.0 \times 10^4$ $M^{-1}$ or more (at 25° C.) for an α1→6 fucose sugar chain No. 405. The fucose α1→6 affinitive lectin is preferably (2) a fucose α1→6 specific lectin which has a characteristic property that the lectin has a binding constant of $1.0 \times 10^4$ $M^{-1}$ or less (at 25° C.) for a sugar chain No. 003 that does not contain α1→6 fucose and a glycolipid-type sugar chain No. 909 that does not contain α1→6 fucose.

9 Claims, 3 Drawing Sheets
Specification includes a Sequence Listing.

METHOD, BIOMARKER AND DIAGNOSTIC AGENT FOR DETECTION OF HIGH-RISK PROSTATE CANCER

TECHNICAL FIELD

The present invention relates to a method, a biomarker and a diagnostic agent for detection of high-risk prostate cancer, and more specifically it relates to the method, the biomarker and the diagnostic agent for detection using lectins.

BACKGROUND ART

Prostate is a reproductive organ present right under a bladder of a male and surrounding his urethra. Cancers that develop in prostates have increased in recent years. Also, numbers of affected persons and PSA screenings have increased, and the number of prostate cancer patients ranks first among male cancers according to 2015 statistics.

Prostate Specific Antigen (hereinafter referred to as "PSA") is an antigen specifically present in a prostate. The PSA includes a complex PSA in which a complex is formed through binding with a protease inhibitor α1-antichymotrypsin (ACT) (prostate-specific antigen-α1-antichymotrypsin complex, hereinafter also referred to as "PSA-ACT"), and a free PSA. In this specification, the PSA means the sum of the complex PSA and the free PSA. In addition, the free PSA is referred to as "fPSA" or "free PSA".

Although a PSA test value in a healthy human blood (hereinafter referred to as blood PSA level) increases with advancing age, the value is generally less than 4 ng/mL. If an abnormally high level of 4 ng/mL or more is measured, prostate cancer is suspected, leading a urologist to early detect prostate cancer.

A group of persons suspected of prostate cancer who have exhibited abnormal PSA levels by the PSA test is subjected to prostate biopsy (test positive) for definitive diagnosis. This biopsy method provides an indicator for obtaining a risk classification indicative of malignancy and severity (stage or progress) of prostate cancer. Risk classification is comprehensively determined by combining three factors, blood PSA level, Gleason score and staging (TNM classification).

The Gleason score (hereinafter also referred to as GS) is an indicator for determining cancer malignancy in microscopic screening of a tissue collected by a prostate needle biopsy. The score is based on histological forms of cancers classified into G1 to G5 patterns from situations of tissues and infiltration (Prostate Cancer Handling Regulation, 4th edition). Since making determination is difficult for the patterns G1 and G2, evaluation is carried out by means of G3 to G5 as described below.

Gleason Pattern

G3: consisting of independent gland duct having a distinct lumen, and infiltrating between existing non-neoplastic ducts.

G4: exhibiting fused gland duct, cribriform gland duct, hypernehromatoid, indistinct gland duct formation.

G5: exhibiting solid growth, trabecular conformation, arcuate growth, comedonecrosis.

Patterns of dominant lesions that are the most frequent lesions (G ○) and accompanying lesions that are the second most frequent lesions (G Δ) are respectively determined, and the sum of their values is taken as the Gleason score (GS=G ○+G Δ). The higher the Gleason score is, the higher the malignancy of the cancer is. Specifically, the relationship between the Gleason score and the malignancy of prostate cancer is as follows.

Gleason Score

GS 6: Relatively slow-developing and well-differentiated type prostate cancer

GS 7: Intermediate-grade Prostate cancer

GS 8 or more: high-grade and poorly-differentiated prostate cancer

Generally, the Gleason scores are often expressed by GS 6 to GS 9. GS 6 (=3+3) is the lowest score. A cancer at GS 6 does not metastasize, and even if an active surveillance method with only follow-up and no treatment is adopted, its prognosis is not different from that with surgery or radiotherapy. Also, there is a controversy that GS 6 need not be called cancer. In the United States, about half of GS 6 patients are treated by the active surveillance treatment. In Japan, surgery and radiotherapy are also performed for cancers at GS6.

The TNM classification is an international standard for indicating staging. Relationship between the classes of the TNM classification and stages is shown in Table 1.

TABLE 1

| Classification | Progress |
|---|---|
| TX | Unevaluable |
| T0 | No cancer is found |
| T1 | Palpation and diagnostic imaging are impossible |
| T2 | T2a: Half or less of single lobe   T2b: Half or more of single lobe   T2c: Exist on Both lobes |
| T3 | T3a: Infiltrate out of capsule (single or both lobes)   T3b: Infiltrate seminal vesicle |
| T4 | Spread to other neighboring organs |
| N0 | No metastasis to lymph nodes |
| N1 | metastasis to lymph nodes |
| M0 | No distant metastasis |
| M1 | Distant metastasis |

Since prostate cancers at GS 7 or more are progressive and metastatic, they fall into a high-risk group requiring early carrying out a treatment such as surgery, radiotherapy and hormone therapy. In the United States, PSA screening is not recommended because it similarly detects non-progressive cancers at GS 6. Also in Japan. "Study on Establishment of Appropriate Cancer Screening Method and Evaluation Method therefor" group of Ministry of Health, Labour and Welfare has made a conclusion that the PSA screening is not recommended for health checks conducted at a public expense, because although it is useful for early diagnosis, its effect for decreasing mortality has not been proved. In the low risk group, the prognosis by follow-up is equivalent to that by treatments such as surgery, radiotherapy and hormone therapy, and thus it is predicted in the future that the high level of the blood PSA at GS 7 or more leads to cancer treatment.

In the current clinical examination algorithm, when an abnormal high level is measured in a blood PSA test, prostate biopsy is essential for obtaining information about the Gleason score and the TNM classification. A biopsy is a diagnostic method in which a tissue is collected from a region suspected of prostate cancer using a prostate needle and the collected tissues and cells are subjected to histopathological test.

In the blood PSA test, prostate cancer (GS 6) requiring no treatment would be determined to be test-positive. The blood PSA level is also increased by aging, prostatic inflammation and hypertrophy. When the blood PSA level is 10 ng/mL or more, a probability of prostate cancer is 50%. When the blood PSA level is 4 to 10 ng/mL, a probability of prostate cancer decreases to 30%. When a patient with a blood PSA level over the standard value is biopsied, probability that prostate cancer cells are detected, and possibility of prostate cancer based on GS 7 to 9 is indicated is about 30%. The remaining 70% include persons without cancer cells and prostate cancer patients at GS 6 or less requiring no surgery. Even if a person is diagnosed to have a high blood PSA level in medical examination and multiphasic health screening, the person does not necessarily have prostate cancer, and thus it is very difficult to identify prostate cancer with current technology.

A highly invasive biopsy is a huge burden to subjects. Development of a simple physiological test method with less invasiveness for subjects is desired. Furthermore, it is desired that the test method correlates with the Gleason score and can predict the Gleason score before biopsy.

Non Patent Document 1 reporting a cancerous change of a PSA sugar chain, describes that a normal PSA includes few double-stranded asparagine-linked sugar chains (N-glycan) and mainly include hybrid-type and high mannose-type sugar chains, meanwhile a prostate cancer-derived PSA includes many branched N-glycans whose terminal binds to a sialic acid at α2-3.

Non-Patent Document 2 reports that when blood fPSAs of patients with prostate cancer or benign prostate hypertrophy having tested blood PSA levels of 4 to 10 ng/mL were measured by ELLA using a UEA-1 lectin having affinity for α1-2-fucose, fucosylation levels of the fPSA in the patients with prostate cancer significantly higher than in the patients with benign prostate hypertrophy were detected.

Patent Document 1 discloses a method for analyzing PSA characterized in that a lectin having affinity for fucose α1-2-galactose residue is brought into contact with a sample possibly containing the PSA to determine an amount of a PSA having affinity for the lectin. In accordance with the method of Patent Document 1, prostate cancer and benign prostate hypertrophy can be distinguished from each other on the basis of the finding that an α1-2-fucosylated PSA increases in a specimen collected from blood of a prostate cancer patient.

PRIOR ART DOCUMENTS

Patent Documents

Patent Document 1: WO 2010/090264 A1 (Method for Analyzing PSA, and Method for Distinguishing between Prostate Cancer and benign prostate disease Employing the Analysis Method)
Patent Document 2: JP Pat. No. 4514163 (fucose α1→6 specific lectin)
Patent Document 3: JP 2011-148736 A (peptide)
Patent Document 4: JP 2011-148735 A (gene)

Non-Patent Documents

Non-Patent Document 1: M. Tajiri et al., "Oligosaccharide profiles of the prostate specific antigen in free and complexed forms from the prostate cancer patient serum and in seminal plasma: a glycopeptide approach.", Glycobiology vol. 18, No. 1, 2008, p 2-8
Non-Patent Document 2: Meriam V. Dwek et al., "A sensitive assay to measure biomarker glycosylation demonstrates increased fucosylation of prostate specific antigen (PSA) in patients with prostate cancer compared with benign prostatic hyperplasia", Clinica Chimica Acta. 41, (2010), p 1935-1939
Non-Patent Document 3: Yuka Kobayashi et al., "A Novel Core Fucose-specific Lectin from the Mushroom *Pholiota squarrosa*", J. Biol. Chem, 2012, 287, p 33973-33982

SUMMARY OF INVENTION

Problem to be Solved

An object of the present invention is to provide a method for providing useful information such as necessity of biopsy before a prostate biopsy to a subject or patient who is suspected of prostate cancer because a blood PSA level has been determined as generally 4 ng/mL or more in a prostate cancer screening by a blood PSA test. Furthermore, the object is to provide an indicator for determining necessity of biopsy to a patient or subject who is difficult to distinguish whether or not prostate cancer is present because a blood PSA level has been determined as 4 ng/mL to lower than 20 ng/mL, particularly 4 ng/mL to 10 ng/mL (gray zone).

Solution to Problem

As a result of intensive studies for solving the above problems, the present inventors have found that when lectin capable of binding to an α1→6 fucose sugar chain is reacted with a specific subject that is a PSA in urine, a detection level of a PSA-lectin complex surprisingly decreases as the malignancy of prostate cancer progresses. The inventors have found that the above problems can be solved on the basis of this finding and completed the present invention.

That is, the present invention provides a method for detecting high-risk prostate cancer, which comprises reacting a PSA contained in a specimen composed of urine collected from a human body suspected of prostate cancer with a lectin capable of binding to an α1→6 fucose sugar chain, wherein the lectin has the following property: (1) it has a binding constant of $1.0 \times 10^4$ $M^{-1}$ or more (at 25° C.) for an α1→6 fucose sugar chain No. 405 having the following structural formula:

[Formula 1]

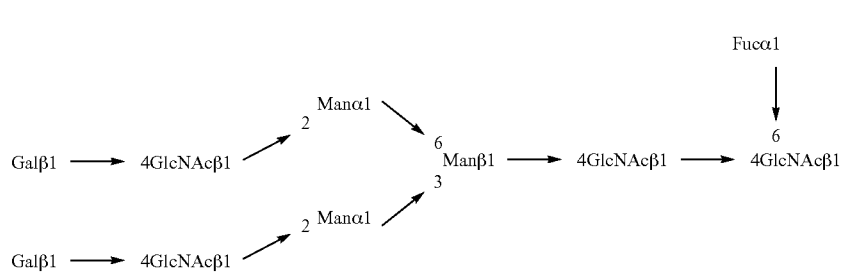

[wherein Gal, GlcNAc, Man and Fuc refer to galactose, N-acetylglucosamine, mannose and fucose respectively]. The structure of the α1→6 fucose sugar chain No. 405 is shown in FIG. 1. The lectin having the property of (1) is referred to as "fucose α1→6-affinitive lectin" in some cases.

In this specification, the "person suspected of prostate cancer" means a person having a blood PSA level abnormally higher than of healthy subjects. The "blood PSA level" means a sum of PSA-ACT and fPSA (total PSA) measured according to a general-purpose measurement method using blood. The "high risk prostate cancer" means advanced prostate cancer, and more specifically, a person exhibits the Gleason score of 7 or more when evaluating the Gleason score, for example.

The methods disclosed in Non Patent Documents 1 and 2 and Patent Document 1 do not detect the PSA bound to an α1→6 fucose so that they are distinctly different from the detection method of the present invention. In addition, it is important that the test subjects in the method of the present invention is "urinary PSA". The methods in the prior art are not directed to a urinary PSA.

In the detection method of the present invention, e.g., when a signal attributed to the reaction of the lectin with the PSA is lower than a signal (reference value) obtained from a person with Gleason score of 6, high-risk prostate cancer is suggested in the person.

The first candidate of the specimen is urine of a person having a blood PSA level of 4 ng/mL or more. Specimens with blood PSA levels of 4 ng/mL or more are suspected of developing prostate cancer.

The second candidate of the specimen is urine of a person having a blood PSA level of lower than 20 ng/mL. Although a patient having a blood PSA level within the above range is determined as test-positive of prostate biopsy, the patient possibly has no prostate cancer and is in the gray zone.

Preferably, the PSA is a free PSA (fPSA).

Preferably, the lectin has the following properties:

(2) it has a binding constant of $1.0 \times 10^4$ $M^{-1}$ or less (at 25° C.) for a sugar chain No. 003 excluding an α1→6 fucose and having the following structural formula:

[Formula 2]

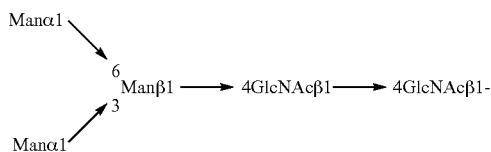

[wherein GlcNAc and Man refer to N-acetylglucosamine and mannose respectively] and for a glycolipid-type sugar chain No. 909 excluding the α1→6 fucose and having the following structural formula:

[Formula 3]

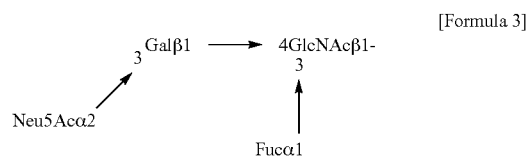

[wherein Gal, GlcNAc, Fuc and Neu5Ac refer to galactose, N-acetylglucosamine, fucose, and N-acetylneuraminic acid respectively]. The structures of the sugar chains No. 003 and No. 909 are shown in FIG. 1 and FIG. 2 respectively. A lectin having not only the property (1) but also the property (2) more specifically binds to the α1→6 fucose sugar chain than a lectin having only the property (1). Hereinafter, a lectin having the properties (1) and (2) is referred to as "fucose α1→6 specific lectin" in some cases.

Preferably, the fucose α1→6 specific lectin further has the following property: (3) it has affinity for the α1→6 fucose sugar chain having sialic acid at a non-reduced terminal of the sugar chain No. 405.

Preferably, the fucose α1→6 specific lectin further has the following property: (4) it has a binding constant of $1.0 \times 10^4$ $M^{-1}$ or more (at 25° C.) for N-linked single-, double-, triple- and/or quadruple-stranded sugar chains bound to the α1→6 fucose.

Examples of the fucose α1→6 affinitive lectin having the property (1) include *Aleuria aurantia* lectin, *Aspergillus oryzae* lectin, *Lens culinaris* lectin, *Pisum sativum* lectin, *Pholiota squarrosa* lectin, *Pholiota terrestris* lectin, *Stropharia rugosoannulata* lectin, *Naematoloma sublateritium* lectin, *Lepista sordida* lectin and *Amanita muscaria* lectin.

The fucose α1→6 specific lectin having not only the property (1) but also the property (2) can be extracted from basidiomycetes belonging to e.g., Strophariaceae, Tricholomataceae, Amanitaceae or Polyporaceae. Specific examples of the fucose α1→6 specific lectin having the properties (1) and (2) include *Pholiota squarrosa* lectin, *Pholiota terrestris* lectin, *Stropharia rugosoannulata* lectin, *Naematoloma sublateritium* lectin, *Lepista sordida* lectin and *Amanita muscaria* lectin.

Preferably, the lectins are labeled.

In the detection method of the present invention, the PSA is preferably detected using the above-described lectin, and one or more kinds of lectins or antibodies. Furthermore, the PSA is preferably detected by an assay using the above-described lectin and an anti-PSA antibody.

Preferably, the anti-PSA antibody is an anti-free PSA antibody (anti-fPSA antibody), and the PSA is a free PSA (fPSA).

Also, the present invention provides a biomarker for diagnosing high-risk prostate cancer, which is composed of a PSA, wherein the PSA can be identified by a lectin capable of binding to an α1→6 fucose sugar chain and having the following property:

(1) it has affinity expressed by a binding constant of $1.0 \times 10^4$ $M^{-1}$ or more (at 25° C.) for the α1→6 fucose sugar chain No. 405 having the following structural formula:

[Formula 4]

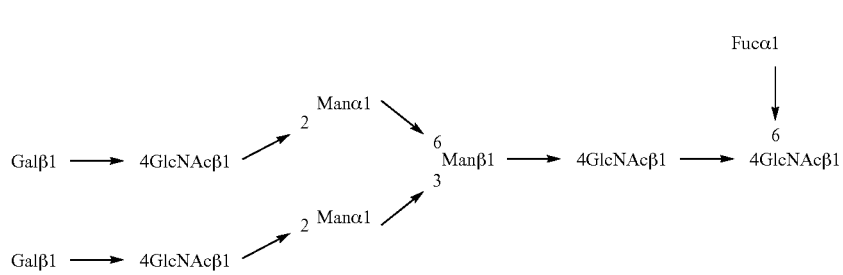

[wherein Gal, GlcNAc. Man and Fuc refer to galactose. N-acetylglucosamine, mannose and fucose respectively]. This biomarker is characterized in that the higher the possibility of prostate cancer is, the lower the detection level as the urinary PSA-lectin complex is, in a person suspected of prostate cancer due to a high blood PSA level.

Also, the present invention provides a biomarker for diagnosing high-risk prostate cancer, which is composed of a PSA, wherein the PSA can be identified by a lectin capable of binding to an α1→6 fucose sugar chain and having the following properties:
(1) it has affinity expressed by a binding constant of $1.0 \times 10^4$ $M^{-1}$ or more (at 25° C.) for an α1→6 fucose sugar chain No. 405 having the following structural formula:

[wherein GlcNAc and Man refer to N-acetylglucosamine and mannose respectively], and for a glycolipid-type sugar chain No. 909 excluding the α1→6 fucose and having the following structural formula:

[Formula 7]

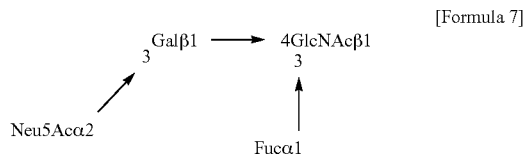

[Formula 5]

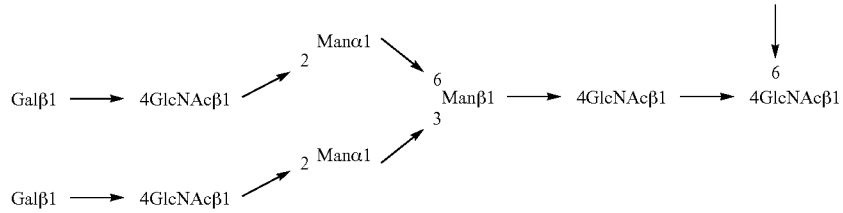

[wherein Gal, GlcNAc, Man and Fuc refer to galactose, N-acetylglucosamine, mannose and fucose respectively] and
(2) it has a binding constant of $1.0 \times 10^4$ $M^{-1}$ or less (at 25° C.) for a sugar chain No. 003 excluding an α1→6 fucose and having the following structural formula:

[Formula 6]

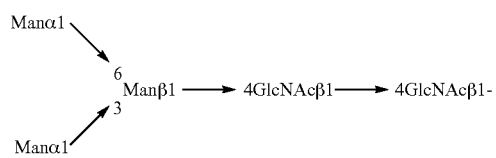

[wherein Gal, GlcNAc, Fuc and Neu5Ac refer to galactose, N-acetylglucosamine, fucose, and N-acetylneuraminic acid respectively]. This biomarker is characterized in that the higher the possibility of prostate cancer is, the lower the detection level as the urinary PSA-lectin complex is, in a person suspected of prostate cancer due to a high blood PSA level.

The PSA is desirably a specimen composed of urine collected from a human body suspected of prostate cancer.

Also, the present invention provides a diagnostic agent for detecting high-risk prostate cancer, containing a lectin capable of binding to an α1→6 fucose sugar chain and having the following property:
(1) it has affinity expressed by a binding constant of $1.0 \times 10^4$ $M^{-1}$ or more (at 25° C.) for an α1→6 fucose sugar chain No. 405 having the following structural formula:

[Formula 8]

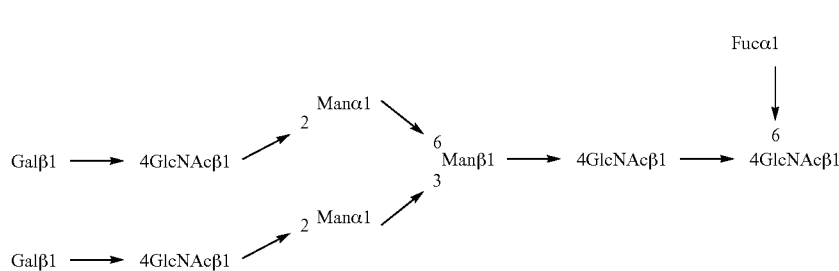

[wherein Gal, GlcNAc, Man and Fuc refer to galactose, N-acetylglucosamine, mannose and fucose respectively], wherein the PSA contained in a specimen composed of urine collected from a human body suspected of prostate cancer is reacted with the lectin.

Also, the present invention provides a diagnostic agent for detecting high-risk prostate cancer, containing a lectin capable of binding to an α1→6 fucose sugar chain and having the following properties:
(1) it has a binding constant of $1.0 \times 10^4$ $M^{-1}$ or more (at 25° C.) for an α1→6 fucose sugar chain No. 405 having the following structural formula:

[Formula 9]

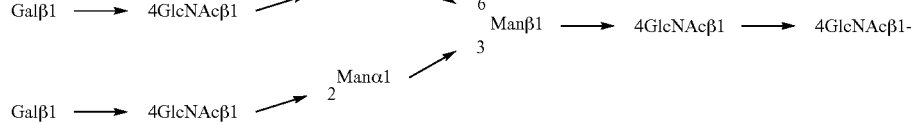

[wherein Gal, GlcNAc, Man and Fuc refer to galactose, N-acetylglucosamine, mannose and fucose respectively], and
(2) it has a binding constant of $1.0 \times 10^4$ $M^{-1}$ or less (at 25° C.) for a sugar chain No. 003 excluding an α1→6 fucose and having the following structural formula:

[Formula 10]

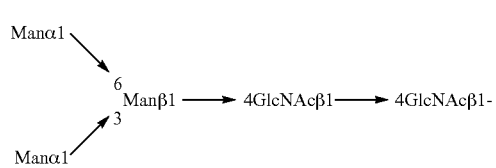

[wherein GlcNAc and Man refer to N-acetylglucosamine and mannose respectively] and for a glycolipid-type sugar chain No. 909 excluding the α1→6 fucose and having the following structural formula:

[Formula 11]

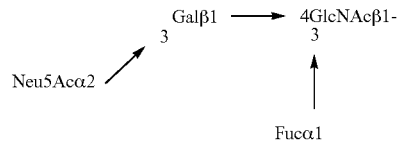

[wherein Gal, GlcNAc. Fuc and Neu5Ac refer to galactose, N-acetylglucosamine, fucose and N-acetylneuraminic acid respectively], wherein the PSA contained in the specimen composed of urine collected from a human body suspected of prostate cancer is reacted with the lectin.

In this specification, the term "diagnostic agent" is used to encompass a form of a kit containing the diagnostic agent. Preferably, the diagnostic agent for detecting prostate cancer further contains an anti-PSA antibody.

Preferably, the diagnostic agent for detecting high-risk prostate cancer further contains an anti-PSA antibody.

Effects of Invention

In a person suspected of prostate cancer due to a high blood PSA level, the higher the risk grade (malignancy) of prostate cancer is, the lower the detection level for the urinary PSA-lectin complex is. In accordance with the detection method of the present invention for detecting the PSA-lectin complex in urea, prostate cancer can be detected with high accuracy. This is in contrast to the fact that high-risk prostate cancer cannot be detected even if using the anti-fPSA antigen, as described in the following Comparative Example.

Conventionally, the Gleason score has been evaluated by biopsy to select patients to be treated. The detection method of the present invention is noninvasive, meanwhile the method makes it possible to properly detect the patients to be essentially treated. The method of the present invention can also provide useful information about the presence or absence of prostate cancer, prior to prostate biopsy on a patient of test positive.

The conventional PSA test is based on measurement of the blood PSA level. Since blood contains only an infinitesimal level of PSA in an ng/mL order, detection accuracy of prostate cancer tends to be low. In addition, the blood PSA level is increased also by benign prostate hypertrophy, prostatic inflammation, etc., and from this point, the detection accuracy is low. Furthermore, in evaluation of the blood PSA level, it is difficult to distinguish prostate cancer with high malignancy from prostate cancer with low malignancy. On the other hand, in the detection method of the present invention, a test subject is the urinary PSA. Urine contains a large amount of PSA in a μg/mL order, and not less than 90% thereof is fPSA. The measurement accuracy in the detection method of the present invention for detecting the urinary PSA is remarkably higher than in the blood PSA test.

For a patient having a blood PSA level in the gray zone, the degree of the detected level is an indicator for determining necessity of the biopsy. Also, for a patient having a blood PSA level remarkably higher than the standard value, the degree of the detected level is an indicator for distinction of the malignancy.

DESCRIPTION OF EMBODIMENTS

Figure 1:
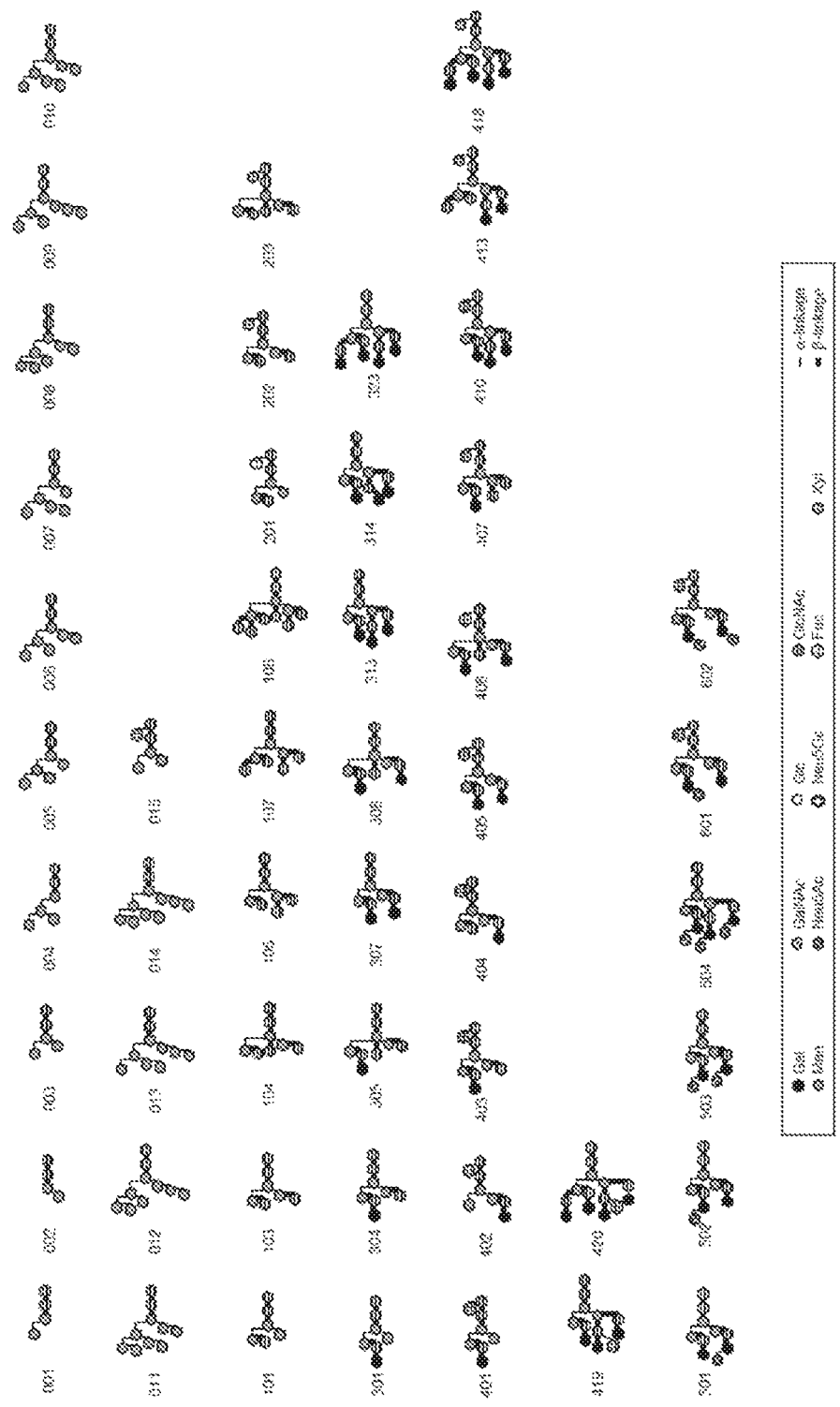
FIG. 1 is a structural drawing of an α1→6 fucose oligosaccharide and a non-α1→6 fucose oligosaccharide.

Embodiments of the present invention will be described in more detail below. The method for detecting high-risk prostate cancer of the present invention comprises reacting a PSA contained in a specimen composed of urine collected from a human body suspected of prostate cancer with a lectin capable of binding to an α1→6 fucose sugar chain.

A first candidate of the subject for the detection method of the present invention is a person who exhibits a blood PSA level of 4 ng/mL or more in a PSA test. Generally, when a subject exhibits a blood PSA level of 4 ng/mL or more, he is suspected of prostate cancer and determined to be test-positive. Test-positive patients include patients who do not need treatment such as GS 6 patients and patients with advanced cancer such as GS 7 to 8 patients. When such a urinary PSA of a person is measured in accordance with the method of the present invention, the detection level of the PSA-lectin complex decreases as the stage of prostate cancer progresses. The method of the present invention can provide an indication for determining necessity of biopsy and information about cancer malignancy of a patient on the basis of the detection level. Particularly, the method of the present invention can provide useful information about the presence or absence of prostate cancer prior to a prostate biopsy for a test-positive patient.

A second candidate of the subject for the detection method of the present invention is particularly a patient who has diagnosed as test-positive because of a blood PSA level of 4 ng/mL or more and exhibits a blood PSA level of lower than 20 ng/mL. A patient with this level of blood PSA value is unlikely to have prostate cancer even if he is test-positive, or he is unlikely to require treatment because of being at GS 6 even if he suffers from prostate cancer. The method of the present invention can provide an indication of determining necessity of biopsy for such a patient.

The PSA measured by the detection method of the present invention is preferably fPSA. About 80% of the blood PSA is PSA-ACT, and about 20% thereof is fPSA. The blood PSA level is a value obtained by measuring the sum of the PSA-ACT and the fPSA (total PSA). On the other hand, not less than 90% of urinary PSA is fPSA. In the blood PSA test, behavior of the PSA-ACT which accounts for the majority is examined, meanwhile in the present invention, behaviour of the major fPSA is examined, and in this point, there is a distinct difference therebetween. In addition, even if a PSA-ACT+fPSA, a PSA-ACT or a fPSA in a specimen collected from a human blood is reacted with a lectin capable of binding to an α1→6 fucose sugar chain, there are problems such as high noise due to serum impurities.

The fucose α1→6-affinitive lectin used in the detection method for the first subject of the present invention is a lectin capable of binding to (i.e. having affinity for) the α1→6 fucose sugar chain.

Such a fucose α1→6 affinitive lectin is defined by the following property: (1) it has affinity expressed by a binding constant of $1.0 \times 10^4$ M$^{-1}$ or more (at 25° C.) for an α1→6 fucose sugar chain No. 405 having the following structural formula:

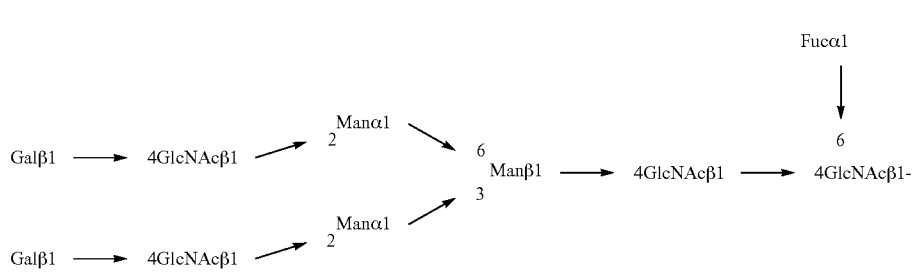

[Formula 12]

Figure 2:
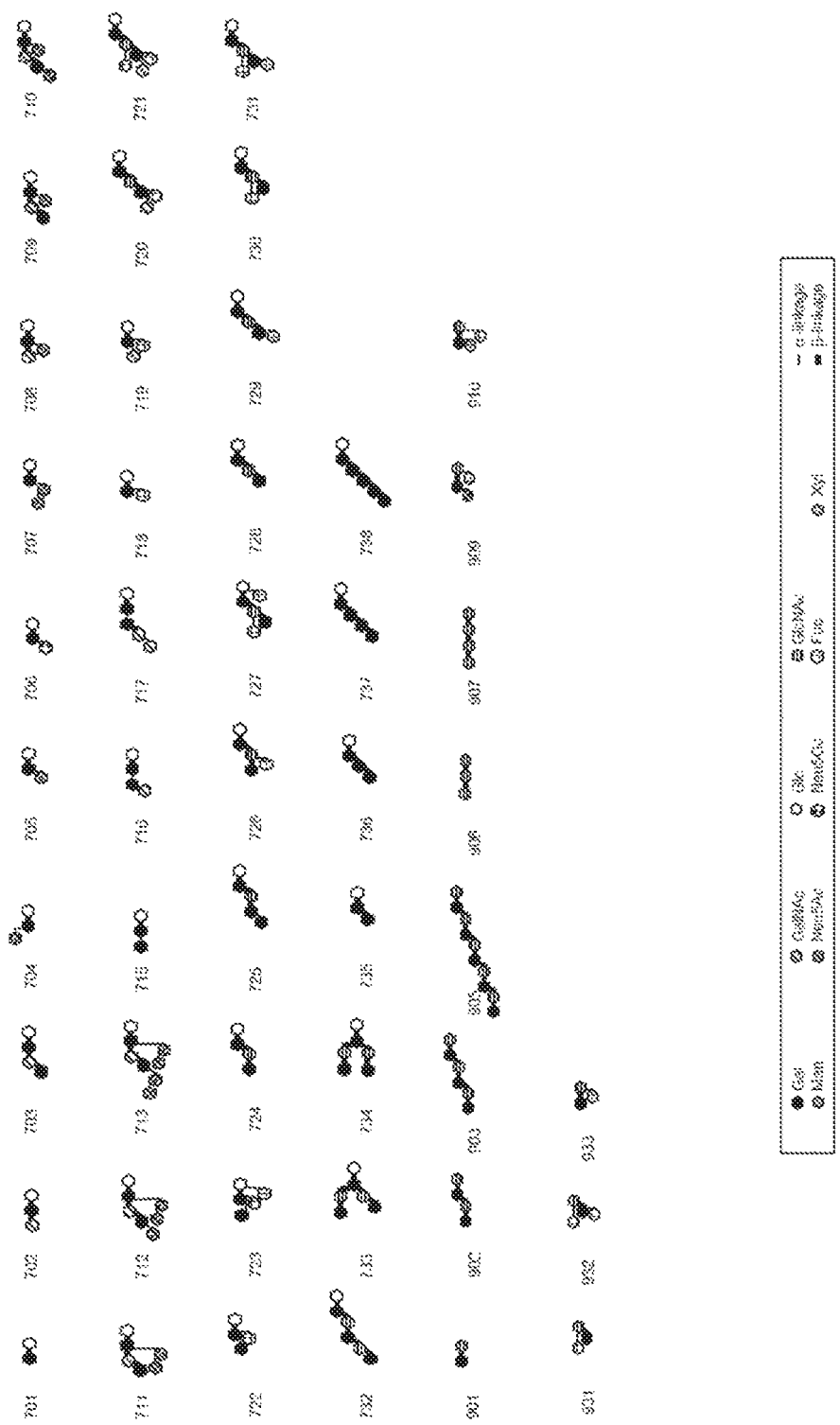
FIG. 2 is another structural drawing of the α1→6 fucose oligosaccharide and the non-α1→6 fucose oligosaccharide.

[wherein Gal, GlcNAc. Man and Fuc refer to galactose. N-acetylglucosamine, mannose and fucose respectively]. Structural drawings of an α1→6 fucose oligosaccharide and a non-α1→6 fucose oligosaccharide are shown in FIGS. 1 and 2. In FIGS. 1 and 2, Gal, GlcNAc, Glc, GalNAc, Man, Fuc, Neu5Ac, Neu5Gc and Xyl refer to galactose, N-acetylglucosamine, glucose, N-acetylgalactosamine, mannose, fucose. N-acetylneuraminic acid, N-glycolylneuraminic acid, and xylose respectively].

Examples of the fucose α1→6 affinitive lectin include *Aleuria aurantia* lectin (AAL). *Aspergillus oryzae* lectin (AOL), *Lens culinaris* lectin (LCL), *Pisum sativum* lectin (PSL), *Pholiota squarrosa* lectin (PhoSL), *Pholiota terrestris* lectin (PTL), *Stropharia rugosoannulata* lectin (SRL), *Naematoloma sublateritium* lectin (NSL), *Lepista sordida* lectin (LSL), *Amanita muscaria* lectin (AML) and the like.

The first or second candidate of the subject for the detection method of the present invention includes a gray zone-risk group. When the candidates in the gray zone are subjects, the lectin for use is preferably a lectin that not only has a high affinity for the α1→6 fucose sugar chain but also specifically binds to the α1→6 fucose sugar chain (fucose α1→6 specific lectin).

The fucose α1→6 specific lectin can be defined by (1) a lower limit of a binding constant for the α1→6 fucose sugar chain, and (2) an upper limit of a binding constant for sugar chains and glycolipid-type sugar chains excluding the α1→6 fucose. More specifically, the α1→6 fucose specific lectin is defined by the following properties: (1) it has affinity expressed by a binding constant of $1.0 \times 10^4$ $M^{-1}$ or more (at 25° C.) for an α1→6 fucose sugar chain No. 405 having the following structural formula:

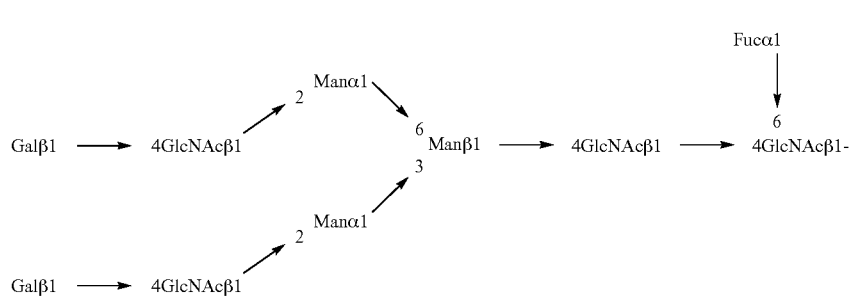

[wherein Gal, GlcNAc, Man and Fuc refer to galactose, N-acetylglucosamine, mannose and fucose respectively] and (2) it has a binding constant of $1.0 \times 10^4$ $M^{-1}$ or less (at 25° C.) for a sugar chain No. 003 excluding the α1→6 fucose and having the following structural formula:

[Formula 14]

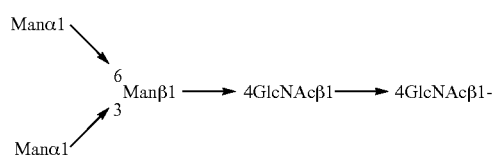

[wherein GlcNAc and Man refer to N-acetylglucosamine and mannose respectively] and for the glycolipid-type sugar chain No. 909 excluding the α1→6 fucose and having the following structural formula:

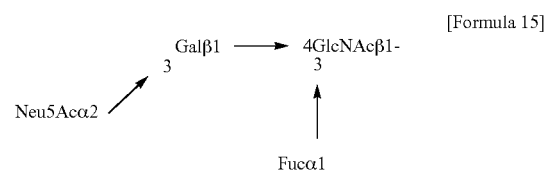

[wherein Gal, GlcNAc, Fuc and Neu5Ac refer to galactose, N-acetylglucosamine, fucose, and N-acetylneuraminic acid respectively].

In this specification, the binding constant means a value measured e.g., by means of a frontal affinity chromatography (FAC method) at an analysis temperature of 25° C. Details of the FAC method are described in Patent Document 2 filed by the present applicant, for example.

The binding constant (at 25° C.) of the lectin for the α1→6 fucose sugar chain No. 405 is preferably $5.0 \times 10^4$ $M^{-1}$ or more, more preferably $1.0 \times 10^5$ $M^{-1}$ or more, still more preferably $2.0 \times 10^5$ $M^{-1}$ or more.

That is, the binding constant (at 25° C.) for the sugar chain No. 003 and glycolipid-type sugar chain No. 909 excluding the α1→6 fucose is generally $1.0 \times 10^3$ $M^{-1}$ or less, preferably $1.0 \times 10^2$ $M^{-1}$ or less, particularly preferably 0.

Furthermore, the fucose α1→6 specific lectin may also have a high affinity for an α1→6 fucose sugar chain having

[Formula 13]

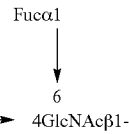

a sialic acid at non-reduced terminal of the sugar chain No. 405. The term "high affinity" means that the binding constant (at 25° C.) is preferably $1.0 \times 10^4$ $M^{-1}$ or more, more preferably $5.0 \times 10^4$ $M^{-1}$ or more, and still more preferably $1.0 \times 10^5$ $M^{-1}$ or more. On the other hand, some conventional lectins have a low affinity for the α1→6 fucose sugar chain having the sialic acid at the non-reduced terminal. Herein, the low affinity means that the binding constant (at 25° C.) is $1.0 \times 10^3$ $M^{-1}$ or less.

The fucose α1→6 specific lectin further has an affinity expressed by a binding constant (at 25° C.) of preferably $1.0 \times 10^4$ $M^{-1}$ or more, more preferably $5.0 \times 10^4$ $M^{-1}$ or more, further preferably $1.0 \times 10^5$ $M^{-1}$ or more for an N-linked single-, double-, triple- and/or quadruple-stranded sugar chain bound to the α1→6 fucose.

The molecular weight of the fucose α1→6 specific lectin based on SDS electrophoresis is usually 4,000 to 40,000, preferably 4,000 to 20,000. Herein, the molecular weight based on SDS electrophoresis is measured according to e.g. a method of Laemmi (Nature, vol. 227, page 680, 1976). The lectin may be generally formed by binding 2 to 10, preferably 2 to 6, more preferably 2 to 3 subunits to each other.

Fucose α1→6 specific lectins obtained from natural products will be outlined. The natural products are exemplified by mushrooms such as basidiomycetes and ascomycetes. Strophariaceae, Tricholomataceae, Polyporaceae and Amanitaceae belong to basidiomycetes. Examples of Strophariaceae include *Pholiota squarrosa, Pholiota terrestris, Stropharia rugosoannulata, Naematoloma sublateritium, Pholiota aurivella, Pholiota adiposa* and the like. Examples of Tricholomataceae include *Lepista sordida* and the like. Examples of Polyporaceae include *Trichaptum elongatum, Microporus vernicipes* and the like. Examples of Amanitaceae include *Amanita muscaria* and the like.

Among these basidiomycetes or ascomycetes, Strophariaceae, Tricholomataceae or Amanitaceae are particularly preferred from the viewpoints of the specificity of the fucose α1→6 specific lectin for recognizing the α1→6 fucose sugar chain and the recovery efficiency of the lectin. Above all. *Pholiota squarrosa* lectin (PhoSL), *Pholiota terrestris* lectin (PTL), *Stropharia rugosoannulata* lectin (SRL). *Naematoloma sublateritium* lectin (NSL), *Lepista sordida* lectin (LSL) and *Amanita muscaria* lectin (AML) are particularly preferable. Amino acid sequences of the PhoSL, SRL, LSL and NSL are shown in Table 2.

The NSL shown in SEQ ID NO: 4 is a lectin that can be extracted from *Naematoloma sublateritium*. The Xaa at the 10th and 17th positions in SEQ ID NO: 4 may be any amino acid residue, but is preferably Cys. The Xaa at the 13th, 14th and 16th positions are Asp/Thr, Ser/Ala and Gln/Lys respectively.

The NSL shown in SEQ ID NO: 5 is also a lectin that can be extracted from *Naematoloma sublateritium*. The Xaa at the 10th and 18th positions in SEQ ID NO: 5 may be any amino acid residue, but is preferably Cys. The Xaa at positions the 14th, 15th and 17th are Asp/Thr, Ser/Ala and Gln/Lys, respectively. Note that SEQ ID NO: 5 can also be said to be a mutant in which one Asn is inserted into the peptide of SEQ ID NO: 4 and furthermore a plurality of amino acids are added to the C terminal.

The fucose α1→6 specific lectin may be not only (a) a protein or peptide consisting of the amino acid sequence shown in any of SEQ ID NOs: 1 to 5, but also (b) a protein or peptide functionally equivalent to the protein or peptide having the amino acid sequence shown in any of SEQ ID NOs: 1 to 5, wherein one or a plurality of amino acids deleted from, inserted into or substituted from the amino acid sequence shown in any of SEQ ID NOs: 1 to 5.

TABLE 2

| Lectin | Amino acid sequence | SEQ ID NO |
|---|---|---|
| PhoSL | Ala-Pro-Val-Pro-Val-Thr-Lys-Leu-Val-Xaa-Asp-Gly-Asp-Thr-Tyr-Lys-Xaa-Thr-Ala-Xaa-Leu-Asp-Xaa-Gly-Asp-Gly-Xaa-Trp-Val-Ala-Gln-Trp-Xaa-Thr-Xaa-Val-Phe-His-Xaa-Gly | 1 |
| SRL | Ala-Pro-Val-Xaa-Val-Thr-Xaa-Leu-Xaa-Xaa-Asp-Gly-Xaa-Ser-Tyr-Lys-Xaa-Thr-Ala-Xaa-Leu-Asp-Tyr-Gly-Asp-Gly-Xaa-Trp-Xaa-Ala-Gln-Trp-Xaa-Xaa-Asn-Val-Phe-His-Xaa | 2 |
| LSL | Xaa-Pro-Val-Xaa-Val-Lys-Xaa-Xaa-Xaa-Xaa-Asp-Gly-Xaa-Thr-Tyr-Xaa-Xaa-Thr-Ala-Xaa-Leu-Xaa-Tyr-Gly-Xaa-Gly-Xaa-Trp-Val-Ala-Xaa-Trp-Ser-Xaa-Ala-Val-Phe-His-Gln-Ser | 3 |
| NSL | Ala-Pro-Val-Pro-Val-Thr-Lys-Leu-Val-Xaa-Asp-Gly-Xaa-Xaa-Phe-Xaa-Xaa-Thr-Ala-Asn-Leu-Asp-Phe-Gly-Asp-Gly-Asn | 4 |
| NSL | Ala-Pro-Val-Pro-Val-Thr-Lys-Leu-Val-Xaa-Asp-Asp-Gly-Xaa-Xaa-Phe-Xaa-Xaa-Thr-Ala-Asn-Leu-Asp-Phe-Gly-Asp-Gly-Asn-Trp-Val-Ala-Gln-Trp-Ser-Thr-Asn-Val-Phe-His-Asn | 5 |

The PhoSL shown in SEQ ID NO: 1 is a lectin that can be extracted from *Pholiota squarrosa*. The Xaa at the 10th and 17th positions in SEQ ID NO: 1 may be any amino acid residue, but is preferably Cys. The Xaa at the 20th, 23rd, 27th, 33rd, 35th and 39th positions are Tyr/Ser, Phe/Tyr, Arg/Lys/Asn, Asp/Gly/Ser, Asn/Ala and Thr/Gln respectively.

The SRL shown in SEQ ID NO: 2 is a lectin that can be extracted from *Stropharia rugosoannulata*. The Xaa at the 10th and 17th positions in SEQ ID NO: 2 may be any amino acid residue, but is preferably Cys. The Xaa at the 4th, 7th, 9th, 13th, 20th, 27th, 29th, 33th, 34th and 39th positions are Pro/Gly, Glu/Lys, Val/Asp, Asn/Asp/Glu, His/Ser, Lys/His, Val/Ile, Gly/Asn/Ser, Ala/Thr and Arg/Thr respectively.

The LSL shown in SEQ ID NO: 3 is a lectin that can be extracted from *Lepista sordida*. The Xaa at the 10th and 17th positions in SEQ ID NO: 3 may be any amino acid residue, but is preferably Cys. The Xaa at the 1st, 4th, 7th, 8th, 9th, 13th, 16th, 20th, 22nd, 25th, 27th, 31st and 34th positions are Ala/Gln, Pro/Lys, Ala/Ser, Met/Ile/Val, Tyr/Thr, Asp/Asn, Lys/Glu, Ala/Asn, Val/Asp/Asn, Asp/Asn, Arg/His/Asn, Gln/Arg and Thr/Val respectively.

Herein, the "functionally equivalent" means that it has affinity expressed by a binding constant (at 25° C.) of $1.0 \times 10^4$ $M^{-1}$ or more, preferably $5.0 \times 10^4$ $M^{-1}$ or more, more preferably $1.0 \times 10^5$ $M^{-1}$ or more, still more preferably $2.0 \times 10^5$ $M^{-1}$ or more for the α1→6 fucose sugar chain No. 405. An example of a protein or peptide variant consisting of the amino acid sequence shown in SEQ ID NO: 4 is a protein or peptide consisting of the amino acid sequence shown in SEQ ID NO: 5.

The fucose α1→6 specific lectin can be extracted and/or purified from a natural product. Methods for obtaining the fucose α1→6 specific lectin derived from a natural product are described in detail in Patent Document 2 filed by the present applicant and Non-Patent document 3 submitted by the present applicant. Herein, *Pholiota terrestris* lectin (PTL) described in Patent Document 2 is replaced by *Pholiota squarrosa* lectin (PhoSL).

Specifically, the method comprises a step of obtaining an aqueous medium extract of basidiomycetes and/or ascomycetes using an aqueous medium as an extraction solvent. The sites for use in these basidiomycetes and/or ascomycetes are preferably fruit bodies. From this extract, a lectin having a molecular weight of generally 4,000 to 40,000, preferably 4,000 to 20.000 as determined by SDS electrophoresis and having affinity expressed by a binding constant (at 25° C.) of generally $1.0 \times 10^4$ $M^{-1}$ or more, preferably $5.0 \times 10^4$ $M^{-1}$ or more, more preferably $1.0 \times 10^5$ $M^{-1}$ or more, and further preferably $2.0 \times 10^5$ $M^{-1}$ or more for the α1→6 fucose sugar chain, is obtained.

The fucose α1→6 specific lectin may also be a peptide or protein obtained by not only extraction from the natural products but also chemical synthesis based on amino acid sequences of a naturally occurring lectin. Furthermore, the chemically synthesized peptide and protein may be a peptide in which one or several amino acids in amino acid sequences of a naturally occurring lectin are substituted with lysine and/or arginine and which has a carbohydrate-binding activity. A synthesis method therefor is described in detail in Patent Document 3 filed by the present applicant.

The fucose α1→6 specific lectin may be not only an extract from the natural product but also a recombinant artificially developed in a known host different from natural origins by using nucleic acids encoding an amino acid sequence of a naturally occurring lectin. A method for developing the recombinant is described in detail in Patent Document 4.

The binding constants (at 25° C.) for various sugar chains (FIGS. 1 and 2) of the fucose α1→6 affinitive lectins AAL, AOL, LCL and PSL are shown in Tables 3 to 6. The binding constants (at 25° C.) for various sugar chains of the α1→6 fucose specific lectins PhoSL, SRL, NSL and LSL are also shown in Tables 3 to 6.

TABLE 3

(I) Binding constant for sugar chains having α1→6 fucose (at 25° C.)

| Sugar chain No. | PhoSL ($M^{-1}$) | SRL ($M^{-1}$) | NSL ($M^{-1}$) | LSL ($M^{-1}$) | AAL ($M^{-1}$) | AOL ($M^{-1}$) | LCL ($M^{-1}$) | PSL ($M^{-1}$) |
|---|---|---|---|---|---|---|---|---|
| 015 | $5.0 \times 10^5$ | $4.9 \times 10^4$ | $3.6 \times 10^4$ | $1.9 \times 10^5$ | $9.1 \times 10^4$ | $1.3 \times 10^4$ | $5.6 \times 10^4$ | $1.2 \times 10^5$ |
| 201 | $4.6 \times 10^5$ | $6.4 \times 10^4$ | $3.8 \times 10^4$ | $2.3 \times 10^5$ | $5.1 \times 10^4$ | $1.2 \times 10^5$ | $5.0 \times 10^5$ | $1.0 \times 10^5$ |
| 202 | $4.0 \times 10^5$ | $6.1 \times 10^4$ | $3.9 \times 10^4$ | $2.3 \times 10^5$ | $5.4 \times 10^4$ | $1.2 \times 10^5$ | $1.1 \times 10^5$ | $4.4 \times 10^4$ |
| 203 | $3.3 \times 10^5$ | $5.2 \times 10^4$ | $3.0 \times 10^4$ | $2.0 \times 10^5$ | $6.6 \times 10^4$ | $1.3 \times 10^5$ | $7.3 \times 10^5$ | $2.5 \times 10^4$ |
| 401 | $3.5 \times 10^5$ | $5.7 \times 10^4$ | $5.1 \times 10^4$ | $3.5 \times 10^5$ | $5.5 \times 10^4$ | $1.4 \times 10^5$ | $4.2 \times 10^4$ | $9.2 \times 10^4$ |
| 402 | $2.0 \times 10^5$ | $4.4 \times 10^4$ | $3.6 \times 10^4$ | $2.0 \times 10^5$ | $1.1 \times 10^4$ | $1.6 \times 10^5$ | $5.9 \times 10^4$ | $4.8 \times 10^4$ |
| 403 | $3.4 \times 10^5$ | $5.6 \times 10^1$ | $5.2 \times 10^4$ | $3.4 \times 10^5$ | $5.2 \times 10^4$ | $1.3 \times 10^5$ | $9.9 \times 10^4$ | $3.8 \times 10^4$ |
| 404 | $3.9 \times 10^5$ | $5.8 \times 10^4$ | $4.3 \times 10^4$ | $3.9 \times 10^5$ | $6.5 \times 10^4$ | $1.5 \times 10^5$ | $5.8 \times 10^4$ | $4.5 \times 10^4$ |
| 405 | $3.2 \times 10^5$ | $5.4 \times 10^4$ | $5.0 \times 10^4$ | $3.2 \times 10^5$ | $5.6 \times 10^4$ | $1.3 \times 10^5$ | $4.7 \times 10^4$ | $3.6 \times 10^4$ |
| 406 | $2.2 \times 10^5$ | $3.8 \times 10^4$ | $2.3 \times 10^4$ | $2.2 \times 10^5$ | $4.7 \times 10^4$ | $1.1 \times 10^5$ | $1.8 \times 10^4$ | $1.3 \times 10^4$ |
| 407 | $2.8 \times 10^5$ | $1.0 \times 10^4$ | N.T | $2.8 \times 10^5$ | $4.5 \times 10^4$ | $1.1 \times 10^5$ | $1.0 \times 10^3$ | $<1.0 \times 10^3$ |
| 410 | $2.2 \times 10^5$ | $3.9 \times 10^4$ | $2.2 \times 10^5$ | $2.2 \times 10^5$ | $3.8 \times 10^4$ | $1.0 \times 10^5$ | $<1.0 \times 10^3$ | $<1.0 \times 10^3$ |
| 413 | $2.8 \times 10^5$ | N.T | $2.8 \times 10^5$ | $2.8 \times 10^5$ | $3.2 \times 10^4$ | $7.9 \times 10^4$ | $<1.0 \times 10^3$ | $<1.0 \times 10^3$ |
| 418 | $2.2 \times 10^5$ | $4.3 \times 10^3$ | $2.2 \times 10^5$ | $2.2 \times 10^5$ | $<1.0 \times 10^3$ | $6.3 \times 10^4$ | $<1.0 \times 10^3$ | $<1.0 \times 10^3$ |
| 601 | $2.4 \times 10^5$ | $1.0 \times 10^4$ | $2.4 \times 10^5$ | $2.4 \times 10^5$ | $6.1 \times 10^4$ | $1.4 \times 10^5$ | $3.0 \times 10^4$ | $3.1 \times 10^4$ |
| 602 | $1.2 \times 10^5$ | $3.2 \times 10^4$ | $1.2 \times 10^5$ | $1.2 \times 10^5$ | $5.2 \times 10^4$ | $1.4 \times 10^5$ | $2.4 \times 10^4$ | $2.9 \times 10^4$ |

N.T: not analyzed

TABLE 4

(2) Binding constant for sugar chains having fucose other than α1→6 fucose (at 25° C.)

| Sugar chain No. | PhoSL ($M^{-1}$) | SRL ($M^{-1}$) | NSL ($M^{-1}$) | LSL ($M^{-1}$) | AAL ($M^{-1}$) | AOL ($M^{-1}$) | LCL ($M^{-1}$) | PSL ($M^{-1}$) |
|---|---|---|---|---|---|---|---|---|
| 419 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 420 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 718 | $<1.0 \times 10^3$ | $<1.0 \times 10^3$ | $<1.0 \times 10^3$ | $<1.0 \times 10^3$ | $6.5 \times 10^4$ | $1.7 \times 10^5$ | $<1.0 \times 10^3$ | $<1.0 \times 10^3$ |
| 719 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 720 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 721 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 722 | $<1.0 \times 10^3$ | $<1.0 \times 10^3$ | $<1.0 \times 10^3$ | $<1.0 \times 10^3$ | $<1.0 \times 10^3$ | $5.6 \times 10^4$ | $<1.0 \times 10^3$ | $<1.0 \times 10^3$ |
| 723 | $<1.0 \times 10^3$ | $<1.0 \times 10^3$ | $<1.0 \times 10^3$ | $<1.0 \times 10^3$ | $3.5 \times 10^4$ | $<1.0 \times 10^3$ | $<1.0 \times 10^3$ | $<1.0 \times 10^3$ |
| 726 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 727 | $<1.0 \times 10^3$ | $<1.0 \times 10^3$ | $<1.0 \times 10^3$ | $<1.0 \times 10^3$ | $1.3 \times 10^5$ | $7.6 \times 10^4$ | $<1.0 \times 10^3$ | $<1.0 \times 10^3$ |
| 728 | $<1.0 \times 10^3$ | $<1.0 \times 10^3$ | $<1.0 \times 10^3$ | $<1.0 \times 10^3$ | $<1.0 \times 10^3$ | $1.2 \times 10^4$ | $<1.0 \times 10^3$ | $<1.0 \times 10^3$ |
| 729 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 730 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 731 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 739 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 909 | $<1.0 \times 10^3$ | $<1.0 \times 10^3$ | $<1.0 \times 10^3$ | $<1.0 \times 10^3$ | $3.1 \times 10^4$ | $4.4 \times 10^4$ | $<1.0 \times 10^3$ | $<1.0 \times 10^3$ |
| 910 | $<1.0 \times 10^3$ | $<1.0 \times 10^3$ | $<1.0 \times 10^3$ | $<1.0 \times 10^3$ | $9.0 \times 10^4$ | $5.6 \times 10^4$ | $<1.0 \times 10^3$ | $<1.0 \times 10^3$ |
| 931 | $<1.0 \times 10^3$ | $<1.0 \times 10^3$ | $<1.0 \times 10^3$ | $<1.0 \times 10^3$ | $<1.0 \times 10^3$ | $9.9 \times 10^4$ | $<1.0 \times 10^3$ | $<1.0 \times 10^3$ |
| 932 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 933 | $<1.0 \times 10^3$ | $<1.0 \times 10^3$ | $<1.0 \times 10^3$ | $<1.0 \times 10^3$ | $2.1 \times 10^5$ | $3.1 \times 10^4$ | $<1.0 \times 10^3$ | $<1.0 \times 10^3$ |

TABLE 5

(3) Binding constant for sugar chains having no fucose (at 25° C.)

| Sugar chain No. | PhoSL (M$^{-1}$) | SRL (M$^{-1}$) | NSL (M$^{-1}$) | LSL (M$^{-1}$) | AAL (M$^{-1}$) | AOL (M$^{-1}$) | LCL (M$^{-1}$) | PSL (M$^{-1}$) |
|---|---|---|---|---|---|---|---|---|
| 001 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 002 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 003 | <1.0 × 10$^3$ | <1.0 × 10$^3$ | <1.0 × 10$^3$ | <1.0 × 10$^3$ | <1.0 × 103 | <1.0 × 10$^3$ | 7.2 × 10$^3$ | 7.8 × 10$^3$ |
| 004 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 005 | <1.0 × 10$^3$ | <1.0 × 10$^3$ | <1.0 × 10$^3$ | <1.0 × 10$^3$ | <1.0 × 103 | 7.3 × 10$^3$ | <1.0 × 10$^3$ | 7.4 × 10$^3$ |
| 006 | <1.0 × 10$^3$ | <1.0 × 10$^3$ | <1.0 × 10$^3$ | <1.0 × 10$^3$ | <1.0 × 103 | <1.0 × 10$^3$ | 1.4 × 10$^3$ | 7.1 × 10$^3$ |
| 007 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | 7.8 × 10$^3$ |
| 008 | <1.0 × 10$^3$ | <1.0 × 10$^3$ | <1.0 × 10$^3$ | <1.0 × 10$^3$ | <1.0 × 103 | 6.9 × 10$^4$ | 1.8 × 10$^4$ | 1.0 × 10$^4$ |
| 009 | <1.0 × 10$^3$ | <1.0 × 10$^3$ | <1.0 × 10$^3$ | <1.0 × 10$^3$ | <1.0 × 103 | <1.0 × 10$^3$ | 1.8 × 10$^4$ | 7.9 × 10$^3$ |
| 010 | <1.0 × 10$^3$ | <1.0 × 10$^3$ | <1.0 × 10$^3$ | <1.0 × 10$^3$ | <1.0 × 103 | <1.0 × 10$^3$ | 1.3 × 10$^4$ | <1.0 × 10$^3$ |
| 011 | <1.0 × 10$^3$ | <1.0 × 10$^3$ | <1.0 × 10$^3$ | <1.0 × 10$^3$ | <1.0 × 103 | <1.0 × 10$^3$ | 1.4 × 10$^4$ | <1.0 × 10$^3$ |
| 012 | <1.0 × 10$^3$ | <1.0 × 10$^3$ | <1.0 × 10$^3$ | <1.0 × 10$^3$ | <1.0 × 103 | <1.0 × 10$^3$ | 2.5 × 10$^4$ | 1.7 × 10$^4$ |
| 013 | <1.0 × 10$^3$ | <1.0 × 10$^3$ | <1.0 × 10$^3$ | <1.0 × 10$^3$ | <1.0 × 103 | <1.0 × 10$^3$ | 1.7 × 10$^4$ | <1.0 × 10$^3$ |
| 014 | <1.0 × 10$^3$ | <1.0 × 10$^3$ | <1.0 × 10$^3$ | <1.0 × 10$^3$ | <1.0 × 103 | <1.0 × 10$^3$ | 1.7 × 10$^4$ | 8.6 × 10$^3$ |
| 101 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 103 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 104 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 105 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 107 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 108 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 301 | <1.0 × 10$^3$ | <1.0 × 10$^3$ | <1.0 × 10$^3$ | <1.0 × 10$^3$ | <1.0 × 103 | 1.8 × 10$^4$ | <1.0 × 10$^3$ | <1.0 × 10$^3$ |
| 304 | <1.0 × 10$^3$ | <1.0 × 10$^3$ | <1.0 × 10$^3$ | <1.0 × 10$^3$ | <1.0 × 103 | 2.0 × 10$^4$ | <1.0 × 10$^3$ | <1.0 × 10$^3$ |
| 305 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 307 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | 2.4 × 10$^3$ |
| 308 | <1.0 × 10$^3$ | <1.0 × 10$^3$ | <1.0 × 10$^3$ | <1.0 × 10$^3$ | <1.0 × 103 | 2.0 × 10$^4$ | <1.0 × 10$^3$ | <1.0 × 10$^3$ |
| 313 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 314 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 323 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 501 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 502 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 503 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |
| 504 | <1.0 × 10$^3$ | <1.0 × 10$^3$ | <1.0 × 10$^3$ | <1.0 × 10$^3$ | <1.0 × 103 | <1.0 × 10$^3$ | <1.0 × 10$^3$ | <1.0 × 10$^3$ |

TABLE 6

(4) Binding constant for sugar chains having no fucose (at 25° C.)

| Sugar chain No. | PhoSL (M$^{-1}$) | SRL (M$^{-1}$) | NSL (M$^{-1}$) | LSL (M$^{-1}$) | AAL (M$^{-1}$) | AOL (M$^{-1}$) | LCL (M$^{-1}$) | PSL (M$^{-1}$) |
|---|---|---|---|---|---|---|---|---|
| 701 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 702 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 703 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 704 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 705 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 706 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 707 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 708 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 709 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 710 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 711 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 712 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 713 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 715 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 716 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 717 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 724 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 725 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 728 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 732 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 733 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 734 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 735 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 736 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 737 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 738 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 901 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 902 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 903 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 905 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |

TABLE 6-continued (4) Binding constant for sugar chains having no fucose (at 25° C.)

| Sugar chain No. | PhoSL (M$^{-1}$) | SRL (M$^{-1}$) | NSL (M$^{-1}$) | LSL (M$^{-1}$) | AAL (M$^{-1}$) | AOL (M$^{-1}$) | LCL (M$^{-1}$) | PSL (M$^{-1}$) |
|---|---|---|---|---|---|---|---|---|
| 906 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |
| 907 | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ | <1.0 × 10$^3$ |

Among the fucose α1→6 affinitive lectins, the AAL and AOL bind to the fucose α1→6 sugar chains (sugar chains No. 015, 201 to 203, and 401 to 418), as well as to the glycolipid-type sugar chain excluding the fucose α1→6 (sugar chains No. 718, 722, 723, 727, 909, 910 and 933). The LCL and PSL bind to the fucose α1→6 sugar chain, as well as to sugar chain excluding the α1→6 fucose (sugar chains No. 003, and 005 to 014). On the other hand, the fucose α1→6 specific lectin such as PhoSL firmly binds to the fucose α1→6 sugar chain and does not bind to the sugar chain excluding the α1→6 fucose at all. Moreover, its coupling constant (at 25° C.) is larger than that of the conventional lectin (coupling constant is 1.0×10$^4$ M$^{-1}$ or more). Furthermore, the binding constant of the fucose α1→6 specific lectin is not decreased even if a sialic acid is added to the fucose α1→6 sugar chain (sugar chains No. 601 and 602). In addition, the fucose α1→6 specific lectin also strongly binds to the triple-strand (sugar chains No. 407 to 413) and the four-strand (sugar chains No. 418) of the fucose α1→6 sugar chain.

Specifically, the detection method of the present invention comprises the following steps:
(A) reacting a urinary PSA collected from a human body suspected of prostate cancer with a lectin capable of binding to an α1→6 fucose sugar chain to obtain a PSA-lectin complex; and
(B) detecting the PSA-lectin complex by an appropriate means.

Preferably, a labeling means is previously incorporated in the lectin for detecting, in the step (B), the PSA-lectin complex obtained in the step (A). The labeling means is not particularly limited, but a known labeling method can be applied, and examples of the method include labeling with a radioisotope, binding of a labelled compound, and the like. Examples of the radioisotope include $^{14}$C, $^3$H and $^{32}$P. Also, an anti-lectin antibody capable of binding to the lectin may be used for detection.

Example of the labelled compound include an enzyme label (horseradish peroxidase, alkaline phosphatase, etc.), a biotin label, a digoxigenin label, a fluorescent label (fluorescein isothiocyanate, CyDye (registered trademark), ethyl 4-aminobenzoate (ABEE), aminopyridine, allophycocyanin, phycoerythrin, etc.), and the like. These labeled compounds can be bound to the lectin by a ordinary method. In particular, the biotin label is preferred from the viewpoint of high sensitivity.

In the above method, the means for detecting the α1→6 fucose sugar chain reacted with the lectin is not particularly limited. As the detection means, ELISA (direct adsorption method, sandwich method and competition method), lectin affinity chromatography, lectin staining, lectin chip, flow cytometry (FACS) method, coagulation method, surface plasmon resonance method (e.g., Biacore (registered trademark) system), electrophoresis, beads, and the like can be used. Several representative detection methods are outlined below.

In the direct adsorption ELISA method, a specimen (urine) is added to a plate and immobilized. Then, the biotin-labeled lectin is added to react the PSA with the lectin. As a secondary labeled compound, an HRP (horseradish peroxidase)-labeled streptavidin solution is added to react the biotin with the streptavidin. Subsequently, a chromogenic substrate for HRP is added to develop color, and the coloring intensity is measured with an absorptiometer. The sugar chain can also be quantified by previously graphing a calibration curve with a standard sample containing a known concentration of the sugar chain.

In the sandwich ELISA method, one or more kinds of lectins and antibodies (e.g. anti-fPSA antibody) or fragments thereof having affinity for the PSA are added to a plate, immobilized, and then a specimen (urine) is added. The antibody may be either a monoclonal antibody or a polyclonal antibody. Then, the biotin-labeled lectin is added to react the urinary PSA with the lectin. This reaction produces the complex of the PSA and the lectin. An HRP-labeled streptavidin solution is added as a secondary labeled compound to react the biotin with the streptavidin. Subsequently, a chromogenic substrate for HRP is added to develop color, and the coloring intensity is measured with an absorptiometer. The α1→6 fucose sugar chain can also be quantified by previously graphing a calibration curve with a known concentration of the standard sample.

The lectin affinity chromatography is an affinity chromatography utilizing the property that a lectin immobilized on a carrier specifically binds to a sugar chain. High throughput can be expected by combining with HPLC.

As a carrier for immobilizing the lectin, gel materials such as agarose, dextran, cellulose, starch and polyacrylamide are commonly used. For these materials, commercial products can be used without special limitation, and exemplified by Sepharose 4B and Sepharose 6B (both of them are manufactured by GE Healthcare Biosciences Corp.). Examples of a column used for the lectin chromatography include a column prepared by immobilizing the lectin on a microplate or a nanowell.

A concentration of a lectin to be immobilized is generally 0.001 to 100 mg/mL, preferably 0.01 to 20 mg/mL. When the carrier is an agarose gel, it is activated with CNBr or the like and then coupled with the lectin. The lectin may be immobilized on a gel into which the activated spacer has been introduced. Furthermore, the lectin may be immobilized on a gel into which a formyl group has been introduced and then reduced with NaCNBH$_3$. Alternatively, a commercial activated gel such as NHS-Sepharose (manufactured by GE Healthcare Biosciences Corp.) may be used.

The specimen (urine) is put in a column, to which subsequently a buffer solution is shed for the purpose of washing. Alternatively, the specimen in the buffer solution is put in the column. The buffer solution can be exemplified by a phosphate buffer solution, a tris buffer solution, a glycine buffer solution and the like, and it has a molar concentration of generally 5 to 500 mM, preferably 10 to 500 mM, and a pH of generally 4.0 to 10.0, preferably 6.0 to 9.0. In addition, it is a buffer solution in which a content of NaCl is generally 0 to 0.5 M, preferably 0.1 to 0.2 M, and a content of $CaCl_2$, $MgCl_2$ or $MnCl_2$ is generally 0 to 10 mM, preferably 0 to 5 mM.

After washing the affinity column, the sugar chain is eluted in a neutral non-modified buffer solution capable of effectively eluting the sugar chain using a desorbent such as sodium chloride and hapten sugar. This buffer solution may be the same as described above. The concentration of the desorbent is preferably 1 to 500 mM, particularly preferably 10 to 200 mM.

In step (B), a signal (reaction value) attributed to the complex of the urinary PSA and the lectin is compared with a signal (reference value) obtained in a patient having a Gleason score of 6 or less, preferably 6 to evaluate the presence or absence of high-risk prostate cancer development and, if cancer has been developed, its malignancy.

The level of the signal (reaction value) attributed to the urinary PSA/lectin complex depends on the type of the lectin and the urinary PSA concentration. Thus, in order to standardize the signal, a calibration curve expressing the relationship between the PSA concentration and the signal value is graphed using a PSA reference standard (known concentration). For each lectin, a reaction value attributed to the anti-fPSA antibody corresponding to the fPSA concentration of 10 ng/mL is taken as 10 U.

If a reaction value between the urinary PSA collected from a patient having a blood PSA level of 4 ng/mL or more (test positive) and the fucose α1→6 affinitive lectin is generally lower than 197 U, the patient probably develops prostate cancer. Conversely, if the reaction value is 197 U or more, the increased blood PSA level of the patient is predicted to be based on benign prostate hypertrophy or prostatic inflammation, or prostate cancer requiring no detailed examination/treatment (GS 6).

If a reaction value between the urinary PSA collected from a patient at gray zone having a blood PSA level of 4 ng/mL or more (test positive) but of less than 20 ng/mL, particularly of 4 ng/mL to 10 ng/mL and the fucose α1→6 affinitive lectin is generally lower than 197 U, the patient probably develops prostate cancer. Conversely, if the reaction value is 197 U or more, the patient is predicted to have benign prostate hypertrophy or prostatic inflammation, or prostate cancer requiring no detailed examination/treatment (GS 6).

If a reaction value between the urine PSA collected from a patient having a blood PSA level of 4 ng/mL or more (test positive) and the fucose α1→6 specific lectin is generally lower than 27 U, the patient probably develops prostate cancer. Conversely, if the reaction value is 27 U or more, the increased blood PSA level of the patient is predicted to be based on benign prostate hypertrophy or prostatic inflammation, or prostate cancer requiring no detailed examination/treatment (GS 6).

If a reaction value between the urinary PSA collected from a patient at gray zone having a blood PSA level of 4 ng/mL or more (test positive) but of lower than 20 ng/mL, particularly of 4 ng/mL to 10 ng/mL and the fucose α1→6 specific lectin is generally lower than 28 U, the patient probably develops prostate cancer. Conversely, if the reaction value is 28 U or more, the patient is predicted to have benign prostate hypertrophy or prostatic inflammation, or prostate cancer requiring no detailed examination/treatment (GS 6).

The present invention also provides a biomarker for diagnosing high-risk prostate cancer, which is composed of a PSA, wherein the PSA can be identified by a lectin capable of binding to an α1→6 fucose sugar chain (fucose α1→6 affinitive lectin) and having the following property:
(1) it has affinity expressed by a binding constant of $1.0×10^4$ $M^{-1}$ or more (at 25° C.) for an α1→6 fucose sugar chain No. 405 having the following structural formula:

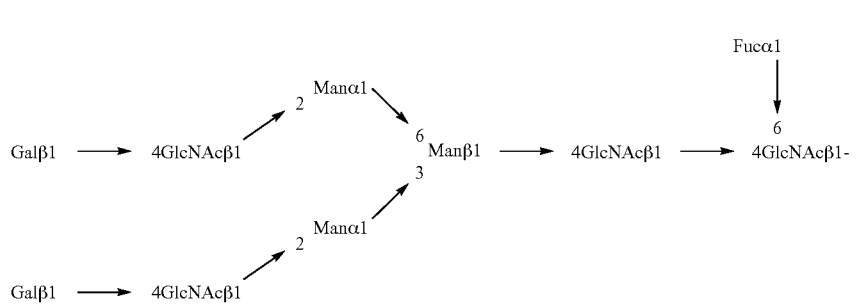

[Formula 16]

[wherein Gal, GlcNAc, Man and Fuc refer to galactose, N-acetylglucosamine, mannose and fucose respectively].

The PSA is preferably contained in a specimen composed of urine collected from a human body suspected of prostate cancer. With the biomarker of the present invention, the higher the possibility of prostate cancer is, the lower the detected level of the complex composed of the PSA and the lectin is.

Also, the present invention provides a biomarker for diagnosing high-risk prostate cancer, which is composed of a PSA, wherein the PSA can be identified by a lectin capable of binding to an α1→6 fucose sugar chain (fucose α1→6 specific lectin) and having the following properties:
(1) it has affinity expressed by a binding constant of $1.0×10^4$ $M^{-1}$ or more (at 25° C.) for an α1→6 fucose sugar chain No. 405 having the following structural formula:

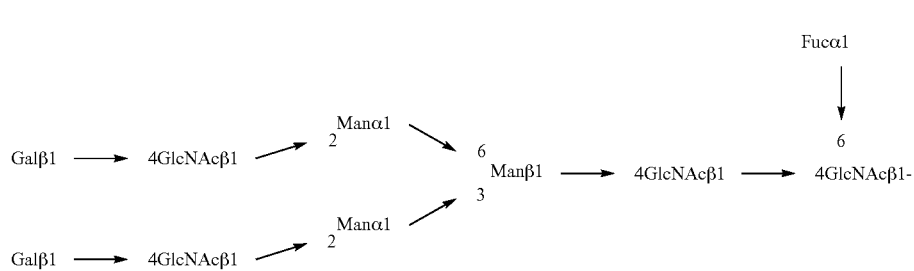

[Formula 17]

[wherein Gal, GlcNAc, Man and Fuc refer to galactose, N-acetylglucosamine, mannose and fucose respectively] and (2) it has a binding constant of $1.0 \times 10^4$ $M^{-1}$ or less (at 25° C.) for a sugar chain No. 003 excluding an α1→6 fucose and having the following structural formula:

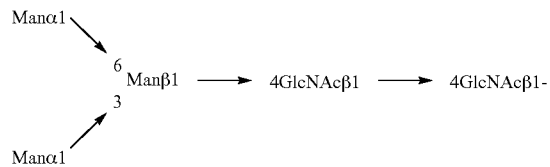

[Formula 18]

[wherein GlcNAc and Man refer to N-acetylglucosamine and mannose respectively] and for a glycolipid-type sugar chain No. 909 excluding the α1→6 fucose and having the following structural formula:

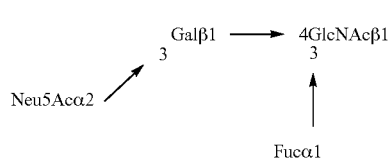

[Formula 19]

[wherein Gal, GlcNAc, Fuc and Neu5Ac refer to galactose, N-acetylglucosamine, fucose, and N-acetylneuraminic acid respectively]. The PSA is preferably contained in a specimen composed of urine collected from a human body suspected of prostate cancer. With the biomarker of the present invention, the higher the possibility of prostate cancer is, the lower the detection level for the complex composed of the PSA and the lectin is.

Also, the present invention provides a diagnostic agent for detecting high-risk prostate cancer, which contains a lectin capable of binding to an α1→6 fucose sugar chain (fucose α1→6 affinitive lectin) and having the following property: (1) it has affinity expressed by a binding constant of $1.0 \times 10^4$ $M^{-1}$ or more (at 25° C.) for an α1→6 fucose sugar chain No. 405 having the following structural formula:

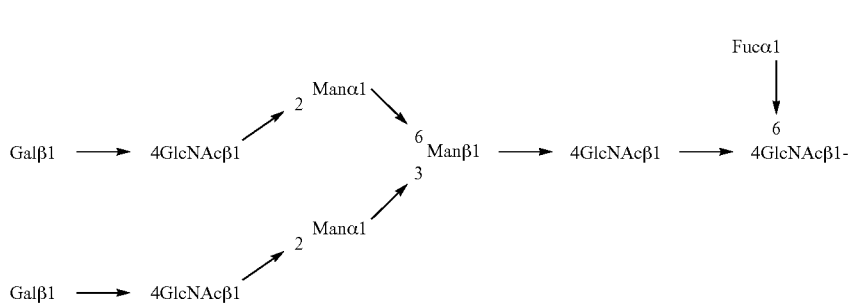

[Formula 20]

[wherein Gal, GlcNAc, Man and Fuc refer to galactose, N-acetylglucosamine, mannose and fucose respectively], wherein PSA contained in a specimen composed of urine collected from a human body suspected of prostate cancer is reacted with the lectin.

Also, the present invention provides a diagnostic agent for detecting high-risk prostate cancer, which contains a lectin capable of binding to an α1→6 fucose sugar chain (fucose α1→6 specific lectin) and having the following property: (1) it has affinity expressed by a binding constant of $1.0 \times 10^4$ $M^{-1}$ or more (at 25° C.) for an α1→6 fucose sugar chain No. 405 having the following structural formula:

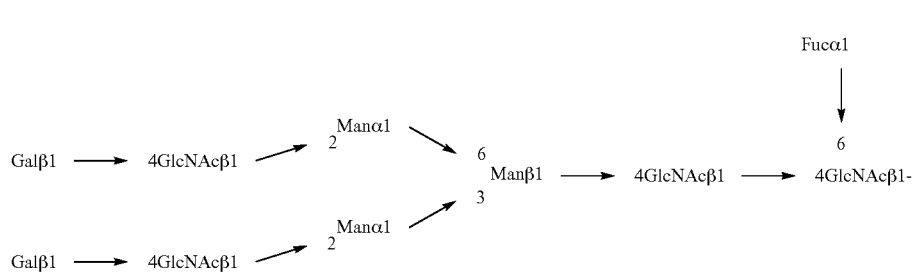

[Formula 21]

[wherein Gal, GlcNAc, Man and Fuc refer to galactose, N-acetylglucosamine, mannose and fucose respectively], and (2) it has a binding constant of $1.0 \times 10^4$ $M^{-1}$ or less (at 25° C.) for a sugar chain No. 003 excluding an α1→6 fucose and having the following structural formula:

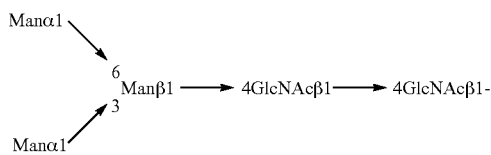

[Formula 22]

[wherein GlcNAc and Man refer to N-acetylglucosamine and mannose respectively], and for a glycolipid-type sugar chain No. 909 excluding the α1→6 fucose and having the following structural formula:

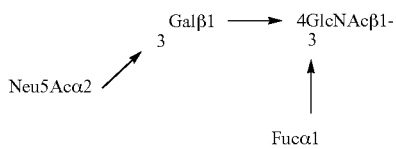

[Formula 23]

[wherein Gal, GlcNAc, Fuc and Neu5Ac refer to galactose, N-acetylglucosamine, fucose and N-acetylneuraminic acid respectively], wherein PSA contained in a specimen composed of urine collected from a human body suspected of prostate cancer is reacted with the lectin.

The diagnostic agent may appropriately include agents generally used for detection kits, such as various labeling compounds, a buffer, a plate, beads and a reaction-stopping liquid. The diagnostic agent preferably includes a reagent for extracting a PSA contained in a specimen obtained from urine (e.g. an anti-PSA antibody or an anti-fPSA antibody, or a fragment or analogue thereof).

EXAMPLES

Hereinafter, the present invention will be described in more detail with reference to Examples of the present invention. However, the present invention is not limited to the following Examples.

Example 1, and Comparative Examples 1 to 3

1. Preparation of Sample

Reagents used for the detection method of the present invention were prepared by the following procedure.

(1) Anti-fPSA Antibody for Solid-Phasing

As anti-fPSA antibody for solid-phasing, an anti-fPSA antibody was purchased from Abcam PLC and used after removing sugar chains in accordance with the method described in Non-Patent Document 3.

(2) Reference Standard

In order to graph a calibration curve, a fPSA (reference standard) was obtained from R&D Systems, Inc.

(3) Anti-fPSA Antibody for Detection

A biotin-labeled anti-fPSA antibody was obtained from R&D Systems, Inc.

(4) Lectin for Detection

As a fucose α1→6 specific lectin used for the method of the present invention, an *Pholiota squarrosa* lectin (PhoSL, SEQ ID NO: 1) was purified from *Pholiota squarrosa* in accordance with the method described in Non-Patent Document 3. The *Pholiota squarrosa* lectin was weighed out, to which a 0.1 M sodium bicarbonate solution was added for dissolution (concentration: 5 mg/mL). A biotinylating reagent dissolved in dimethylsulfoxide was added to the lectin solution and reacted. The reaction solution was subjected to solvent substitution with water using ultrafiltration (3 K). This solution was lyophilized to obtain a biotin-labeled PhoSL. In addition, a biotin-labeled *Aleuria aurantia* lectin (biotin-labeled AAL, manufactured by J-OIL MILLS, Inc.) was prepared as a fucose α1→6 affinitive lectin.

(5) Reagents and the Like for Use (5-1) Phosphate Buffered Saline (PBS)

5.75 g of disodium hydrogenphosphate, 1.0 g of potassium dihydrogenphosphate, 1.0 g of potassium chloride, and 40.0 g of sodium chloride were dissolved in 5 L of water to obtain PBS.

(5-2) 3% Bovine Serum Albumin (BSA)/PBS 3 g of bovine serum albumin (BSA, manufactured by Sigma-Aldrich Co. LLC) was dissolved in 100 mL of PBS to obtain a PBS solution with a BSA concentration of 3% (hereinafter referred to as 3% BSA/PBS).

(5-3) 1% Bovine Serum Albumin (BSA)/PBS 1 g of bovine serum albumin (BSA, manufactured by Sigma-Aldrich Co. LLC) was dissolved in 100 mL of PBS to obtain a PBS solution with a BSA concentration of 1% (hereinafter referred to as 1% BSA/PBS).

(6) Subject Sample

Informed consent was gotten from patients with prostate cancer at Osaka University Hospital, and then their collected urine was used as subject samples. Information on a blood PSA level and a Gleason score of a patient were added to each specimen. The contents of the subject samples are shown in Table 7.

TABLE 7

| Name of subject samples | n | Blood PSA value (Median value) (ng/mL) | Gleason score |
|---|---|---|---|
| Negative | 20 | 3.96~19.7 (8.32) | — |
| GS6 | 20 | 2.99~126.8 (6.83) | 6 |
| GS7 | 20 | 5.08~178 (9.45) | 7 |
| GS8-9 | 18 | 4.33~606 (14.03) | 8-9 |

The "Negative" refers to a group in which the blood PSA level was high but prostate cancer was not detected in the prostate biopsy. However, it is predicted that prostate cancer is included with a probability of 5 to 310% even in the "Negative", in light of problems of the biopsy sensitivity.

2. Procedure of Sandwich ELISA
(1) Antibody Immobilization
The anti-fPSA antibody from which sugar chains had been removed was diluted to 1 µg/mL with PBS. 50 µL of this diluted solution was added to each well of an ELISA plate and allowed to stand at 37° C. for 12 hours, and then the additive solution was discarded.
(2) Washing
250 µL of PBS containing 0.1% Tween 20 (product name: polyoxyethylene sorbitan monolaurate, manufactured by Nacalai Tesque. Inc.) was added to each well, and then the additive solution was discarded. This manipulation was repeated three times in total.
(3) Blocking
200 µL of PBS containing 3% BSA was added to each well and allowed to stand at 37° C. for 1 hour, and then the additive solution was discarded.
(4) Washing
250 µL of PBS containing 0.1% Tween 20 was added to each well, and the additive solution was discarded. This manipulation was repeated three times in total.
(5) Antigen-Antibody Reaction
50 µL of urine of the subject was added to each well and allowed to stand at room temperature for 1 hour, and then the additive solution was discarded.
(6) Washing
250 µL of PBS containing 0.1% Tween 20 was added to each well, and then the additive solution was discarded. This manipulation was repeated three times in total.
(7) Reaction of Anti-fPSA Antibody or Lectin
50 µL of a biotin-labeled anti-fPSA antibody diluted to 1 µg/mL with PBS was added to each well and allowed to stand at 4° C. for 30 minutes, and then the additive solution was discarded. Likewise, 50 µL of a biotin-labeled PhoSL or a biotin-labeled AAL diluted to 1 µg/mL with PBS containing 1% BSA solution was added to each well and allowed to stand at 4° C. for 30 minutes, and then the additive solution was discarded.
(8) Washing
250 µL of PBS containing 0.1% Tween 20 was added to each well, and the additive solution was discarded. This manipulation was repeated three times in total.
(9) HRP-Labeled Streptavidin Reaction
50 µL of a horseradish peroxidase (HRP)-labeled streptavidin solution (manufactured by Vector Laboratories, Inc., concentration: 1 µg/mL, in PBS containing 1% BSA) was added to each well and allowed to stand at room temperature for 1 hour, and then the additive solution was discarded.

(10) Washing
250 µL of PBS containing 0.1% Tween 20 was added to each well, and the additive solution was discarded. This manipulation was repeated three times in total.
(11) Coloring Reaction
50 µL of chromogenic substrate for HRP (product name: TMB, manufactured by Kirkegaard & Perry Laboratories, Inc.) was added to each well and allowed to stand at room temperature for 15 minutes.
(12) Stopping of Reaction
50 µL of 1 M sulfuric acid was added to terminate the reaction.
(13) Absorbance Measurement
Absorbance (Ab) at 450 nm and 630 nm was measured using a plate reader, and a value calculated by subtracting the $Ab_{630}$ from the $Ab_{450}$ was obtained as a reaction value ($Ab_{450\text{-}630}$).

Unit calculation was carried out as follows. Instead of the urine of the subject, a reference standard (fPSA) was prepared with PBS so that the concentration is 0 to 40 ng/ml, and a calibration curve was graphed by plotting signals (reaction values) with the biotin-labeled anti-fPSA antibody. A reaction value ($Ab_{450\text{-}630}$) corresponding to the fPSA concentration of 10 ng/mL was calculated using the calibration curve. The reaction value ($Ab_{450\text{-}630}$) of the biotin-labeled anti-fPSA antibody corresponding to the fPSA concentration of 10 ng/mL was taken as 10 U. As for the detection with the biotin-labeled PhoSL or biotin-labeled AAL, the same reaction value ($Ab_{450\text{-}630}$) as in the case of the above 10 U was taken as 10 U.

The PhoSL reaction values of the urinary fPSA, the AAL reaction values of the urinary fPSA, the anti-fPSA antibody reaction values of the urinary fPSA, and blood PSA values (PSA test values) in the two groups, the negative and GS 6 group and the GS 7 to 9 group are shown in Table 8.

The relationship between reactivity of the urinary fPSA with the PhoSL or the AAL and the Gleason score was further investigated. Classification based on the Gleason score, number of persons to be measured in each group, and PhoSL and AAL reaction values are shown in Table 8. For comparison, the reaction values of the urinary fPSA with the anti-fPSA antibody (Comparative Example 1) and the blood PSA values (Comparative Example 2) are additionally described.

TABLE 8

| Group | n | Example 1 PhoSL reaction value[X] (U) | Example 2 AAL reaction value[X] (U) | Comparative Example 1 Anti-fPSA antibody reaction value[X] (U) | Comparative Example 2 Blood PSA value[X] (ng/mL) |
|---|---|---|---|---|---|
| Negative | 20 | 54.10 | 288.6 | 156.1 | 8.360 |
|  |  | 44.75 | 271.3 | 128.9 | 7.800 |
|  |  | 26.86 | 145.0 | 107.3 | 4.014 |
| GS6 | 20 | 37.29 | 282.4 | 132.4 | 17.39 |
|  |  | 31.13 | 255.6 | 122.4 | 6.825 |
|  |  | 19.04 | 150.5 | 119.1 | 29.36 |
| GS7 | 20 | 33.00 | 221.1 | 122.4 | 23.05 |
|  |  | 28.96 | 194.4 | 102.3 | 9.635 |
|  |  | 16.66 | 97.38 | 96.46 | 38.98 |
| GS8-9 | 18 | 24.63 | 190.8 | 63.29 | 75.75 |
|  |  | 23.63 | 160.2 | 55.49 | 12.91 |
|  |  | 11.78 | 143.0 | 52.57 | 156.4 |

[X]Reaction value or blood PSA value
Upper line: Mean value
Middle line: Median value
Lower line: Standard deviation In Table 8, the blood PSA value tends to increase as the Gleason score increases, but this is not so significant. The reaction value of the urinary fPSA with the anti-fPSA antibody tends to decrease as the Gleason score increases, but this is not so significant. On the other hand, the PhoSL and AAL reaction values tend to significantly decrease as the Gleason score increases. In particular, the PhoSL reaction value was proven to clearly decrease.

When the lectin reaction values in Examples 1 and 2 are standardized, it is predicted that the Gleason score is low if the reaction value of the PhoSL or the AAL is not lower than the standard value of 27 U or 197 U. Thus, in the case of a patient in the gray zone-risk group, if the lectin reaction value is not lower than the standard value, it is suggested that biopsy is not needed. On the other hand, if the lectin reaction value is lower than the standard value, it is predicted that the Gleason score is high. For the patients in the gray zone-risk group, if the lectin reaction value is lower than the standard value, the Gleason score is high, suggesting the need of prostate biopsy for detailed diagnosis.

Figure 3:
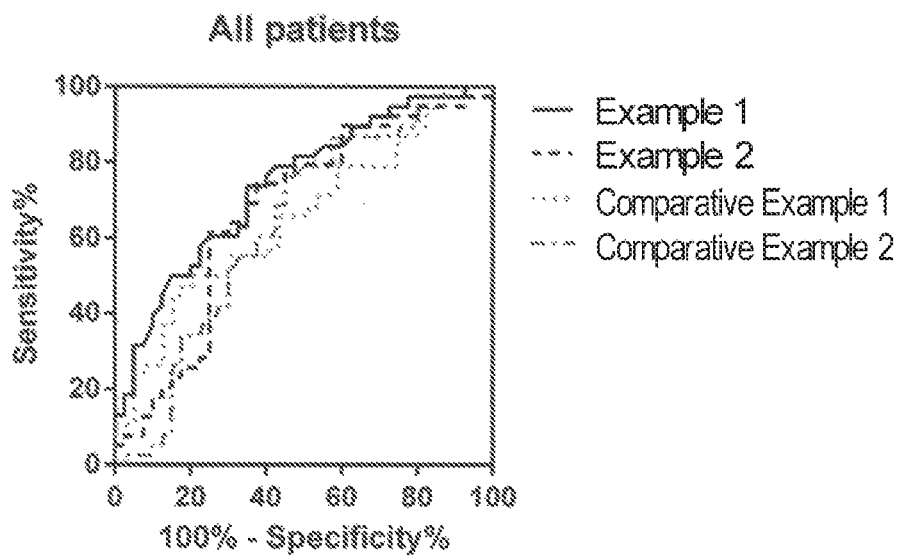
FIG. 3 illustrates an ROC curve graphed from the results of Examples 1 and 2 and Comparative Examples 1 and 2.

From the above results, a ROC curve (Receiver Operatorating Characteristic curve) was graphed. The result is shown in FIG. 3.

An AUC (area under the ROC curve) obtained from the ROC curve is shown in Table 9. The AUC value ranges 0.5 to 1.0, and the closer to 1.0 the value is, the higher the prediction ability and diagnostic ability are.

TABLE 9

|  | Example 1 | Example 2 | Comparative Example 1 | Comparative Example 2 |
|---|---|---|---|---|
| AUC | 0.7405 | 0.6712 | 0.6349 | 0.6505 |

From the results of the ROC curve, it was found that the PhoSL in Example 1 and the AAL of Example 2 have higher specificity for detecting prostate cancer than the anti-fPSA antibody in Comparative Example 1, and particularly the PhoSL has higher specificity.

Examples 3 and 4, and Comparative Examples 3 and 4

The results of Examples 1 and 2 and Comparative Examples 1 and 2 were organized exclusively for the subjects having the blood PSA levels of lower than 20 ng/mL (hereinafter referred to as "<20 ng/mL"). The PhoSL reaction value of the urinary fPSA (Example 3), the AAL reaction value of the urinary fPSA (Example 4), and the anti-fPSA antibody reaction value of the urine fPSA (Comparative Example 3), as well as the blood PSA value (Comparative Example 4) in the two groups, the negative and GS 6 group and the GS 7 to 9 group (with the proviso of the blood PSA value <20 ng/mL) are shown in Table 10.

The relationship between the reactivity of the urinary fPSA with the PhoSL or the AAL and the Gleason score was investigated in detail exclusively for the group in which the blood PSA value is positive and <20 ng/mL. Classification in the Gleason score, number of subjects in each group, and the PhoSL and AAL reaction values are shown in Table 10. For comparison, the anti-fPSA antibody reaction values and the blood PSA values in each group are also shown in Table 10.

TABLE 10

| Group | n | Example 3 PhoSL reaction value$^X$ (U) | Example 4 AAL reaction value$^X$ (U) | Comparative Example 3 Anti-fPSA antibody reaction value$^X$ (U) | Comparative Example 4 Blood PSA value$^X$ (ng/mL) |
|---|---|---|---|---|---|
| Negative | 19 | 57.9 | 321.6 | 156.1 | 8.36 |
|  |  | 42.8 | 304.1 | 128.9 | 7.8 |
|  |  | 26.86 | 165.7 | 107.3 | 4.141 |
| GS6 | 16 | 38.5 | 276.5 | 144.2 | 6.93 |
|  |  | 31.1 | 241.4 | 125.3 | 6.69 |
|  |  | 21.62 | 155.1 | 129.5 | 2.425 |
| GS7 | 15 | 34.3 | 224.9 | 130.7 | 9.01 |
|  |  | 30.4 | 194.4 | 104.8 | 8.3 |
|  |  | 16.97 | 109.3 | 105.2 | 3.458 |
| GS8-9 | 12 | 24.8 | 181.2 | 67.89 | 10.05 |
|  |  | 22.2 | 142.0 | 63.56 | 7.77 |
|  |  | 12.15 | 154 | 56.88 | 5.367 |

$^X$Reaction value or blood PSA value
Upper line: Mean value
Middle line: Median value
Lower line: Standard deviation In Table 10, no correlation was found between the blood PSA value and the Gleason score in Comparative Example 4. Although the anti-fPSA antibody reaction value in Comparative Example 3 decreases as the Gleason score increases, there is no significant difference. On the other hand, the PhoSL reaction value in Example 3 and the AAL reaction value in Example 4 significantly decrease as the Gleason score increases. Consequently, when the subject is restricted to the gray zone group having the blood PSA value of not lower than 4 ng/mL (test positive for biopsy) to lower than 20 ng/mL, it is also effective to detect the urinary PSA by the lectin capable of binding to the α1→6 fucose sugar chain.

Comparing the PhoSL reaction value with the AAL reaction value, the PhoSL reaction value can be more clearly distinguished than the AAL reaction value. It can be said that the fucose α1→6 specific lectin such as the PhoSL is most effective for the gray zone group having the blood PSA value of <20 ng/mL.

When the lectin reaction values in Examples 3 and 4 are standardized, it is predicted that the Gleason score is low if the reaction value of the PhoSL or the AAL is not lower than the standard value of 28 U or 197 U. Thus, in a case of a patient in the gray zone-risk group, if the lectin reaction value is not lower than the standard value, it is suggested that biopsy is not needed. On the other hand, if the lectin reaction value is lower than the standard value, it is predicted that the Gleason score is high. For the patients in the gray zone-risk group, if the lectin reaction value is lower than the standard value, the Gleason score is high, suggesting the need of prostate biopsy for detailed diagnosis.

Exclusively for groups having the blood PSA value of less than 20 ng/mL, it was found that the reaction values with the PhoSL (Example 3) and the AAL (Example 4) in the GS 7 to 9 groups were lower than in the negative and GS 6 group. With the anti-fPSA antibody (Comparative Example 3) and the blood PSA (Comparative Example 4), such difference was not observed. From this, for the risk group having the blood PSA value of not lower than 4 ng/mL to lower than 20 ng/mL (patients in gray zone), the measured reactivity of the PhoSL or the AAL to the urinary fPSA can be used as an indicator for determining necessity of prostate biopsy.

Figure 4:
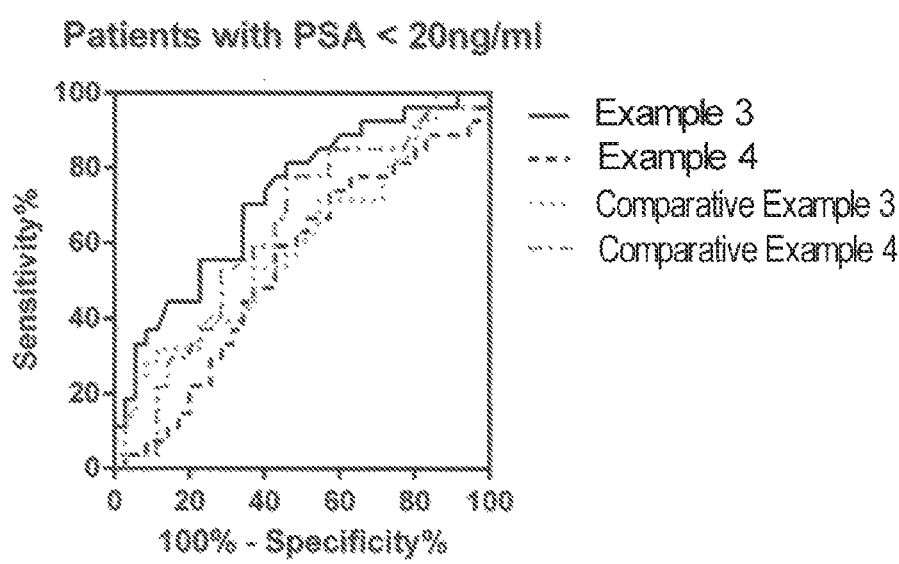
FIG. 4 illustrates an ROC curve graphed from the results of Examples 3 and 4 and Comparative Examples 3 and 4.

Based on the above results, an ROC curve was graphed. The results are shown in FIG. 4. In addition, an AUC (area under the ROC curve) obtained from the ROC curve is shown in Table 11.

TABLE 11

|  | Example 3 | Example 4 | Comparative Example 3 | Comparative Example 4 |
|---|---|---|---|---|
| AUC | 0.7254 | 0.5429 | 0.6349 | 0.5990 |

From the AUC of Table 11, it can be seen that the specificity for detecting prostate cancer is highest on the reaction value of the urinary fPSA with the PhoSL in Example 3.

When comparing the difference of the AUC between Example 1 and Comparative Example 2 (Table 9) with the difference of the AUC between Example 3 and Comparative Example 4 (Table 11), the difference in Table 11 is larger. From this, it can be said that the fucose α1→6 specific lectin like the PhoSL is most effective for the patients in gray zone having the blood PSA value of <20 ng/mL.

The invention claimed is:

1. A method for detecting high-risk prostate cancer, the method comprising:

reacting a PSA contained in a specimen composed of urine collected from a human body suspected of prostate cancer with a lectin capable of binding to an α1→6 fucose sugar chain;

comparing a reaction value of a signal attributed to the reaction of the PSA with the lectin with a reference value of a signal attributed to a reaction of a PSA contained in a specimen composed of urine collected from a person with Gleason score of 6 with the lectin;

evaluating a presence or an absence of the high-risk prostate cancer in the human body based on a result of the comparison between the reaction value and the reference value; and detecting the presence of the high-risk prostate cancer in the human body based on the result of the comparison that indicates that the reaction value is lower than the reference value, wherein the lectin is at least one selected from a group consisting of Aleuria aurantia lectin and Pholiota squarrosa lectin.

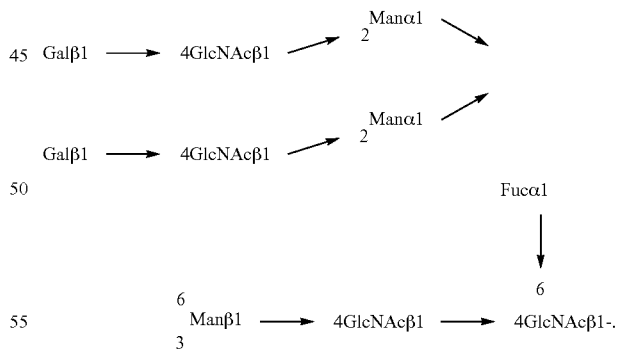

2. The method for detecting high-risk prostate cancer according to claim 1, wherein the specimen is urine of a person having a blood PSA level of 4 ng/mL or more.

3. The method for detecting high-risk prostate cancer according to claim 2, wherein the specimen is urine of a person having a blood PSA level of lower than 20 ng/mL.

4. The method for detecting high-risk prostate cancer according to claim 1, wherein
the PSA is a free PSA (fPSA).

5. The method for detecting high-risk prostate cancer according to claim 1, wherein the lectin is Pholiota squarrosa lectin.

6. The method for detecting high-risk prostate cancer according to claim 1, wherein
the lectin is labeled.

7. The method for detecting high-risk prostate cancer according to claim 1, wherein
the PSA is detected using the lectin, and one or more kinds of lectins or antibodies.

8. The method for detecting high-risk prostate cancer according to claim 7, wherein the PSA is detected by an assay using the lectin and an anti-PSA antibody.

9. The method for detecting high-risk prostate cancer according to claim 8, wherein the anti-PSA antibody is an anti-free PSA antibody (anti-fPSA antibody), and
the PSA is a free PSA (fPSA).

* * * * *

UNITED STATES PATENT AND TRADEMARK OFFICE
CERTIFICATE OF CORRECTION

PATENT NO. : 11,226,334 B2  
APPLICATION NO. : 16/073217  
DATED : January 18, 2022  
INVENTOR(S) : Yuka Kobayashi et al.

Page 1 of 1

It is certified that error appears in the above-identified patent and that said Letters Patent is hereby corrected as shown below:

In the Claims

Column 40, Lines 45 to 55, (Claim 1), delete:

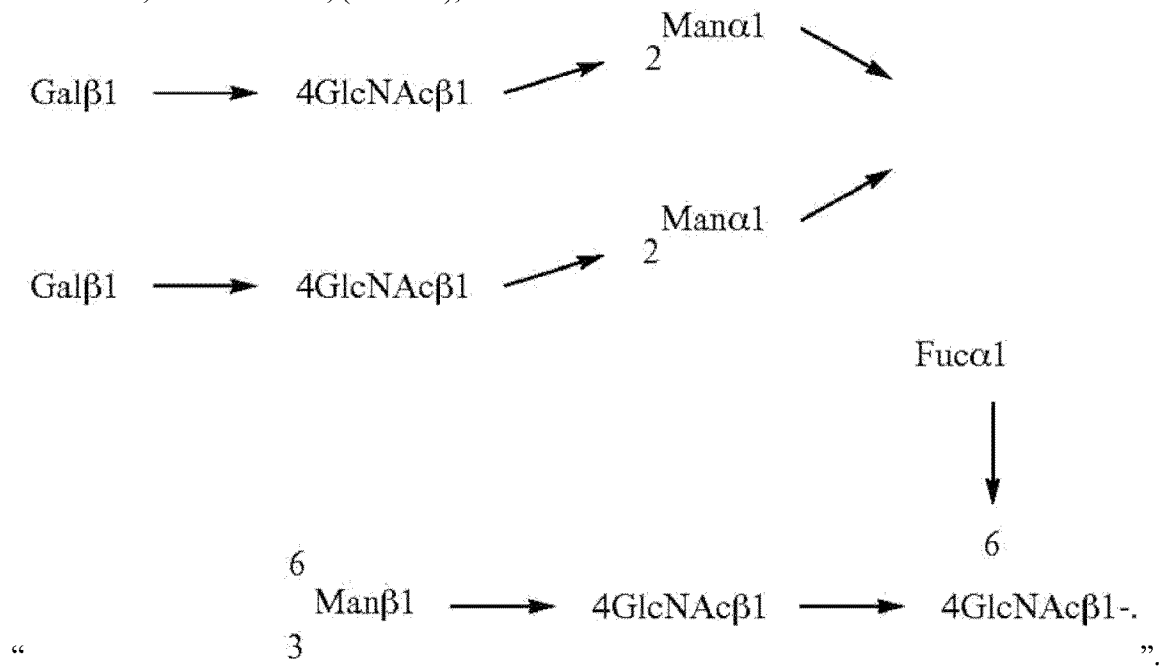

Signed and Sealed this  
Thirty-first Day of May, 2022

Katherine Kelly Vidal  
*Director of the United States Patent and Trademark Office*

SEQUENCE LISTING

```
<160> NUMBER OF SEQ ID NOS: 5

<210> SEQ ID NO 1
<211> LENGTH: 40
<212> TYPE: PRT
<213> ORGANISM: Pholiota squarrosa
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (17)..(17)
<223> OTHER INFORMATION: X stands for any amino acid, preferably Cys.
<220> FEATURE:
<221> NAME/KEY: MISC_FEATURE
<222> LOCATION: (20)..(20)
<223> OTHER INFORMATION: X stands for Tyr/Ser.
<220> FEATURE:
<221> NAME/KEY: MISC_FEATURE
<222> LOCATION: (23)..(23)
<223> OTHER INFORMATION: X stands for Phe/Tyr.
<220> FEATURE:
<221> NAME/KEY: MISC_FEATURE
<222> LOCATION: (27)..(27)
<223> OTHER INFORMATION: X stands for Arg/Lys/Asn.
<220> FEATURE:
<221> NAME/KEY: MISC_FEATURE
<222> LOCATION: (33)..(33)
<223> OTHER INFORMATION: X stands for Asp/Gly/Ser.
<220> FEATURE:
<221> NAME/KEY: MISC_FEATURE
<222> LOCATION: (35)..(35)
<223> OTHER INFORMATION: X stands for Asn/Ala.
<220> FEATURE:
<221> NAME/KEY: MISC_FEATURE
<222> LOCATION: (39)..(39)
<223> OTHER INFORMATION: X stands for Thr/Gln.

<400> SEQUENCE: 1

Ala Pro Val Pro Val Thr Lys Leu Val Xaa Asp Gly Asp Thr Tyr Lys
1               5                   10                  15

Xaa Thr Ala Xaa Leu Asp Xaa Gly Asp Gly Xaa Trp Val Ala Gln Thr
            20                  25                  30

Xaa Thr Xaa Val Phe His Xaa Gly
        35                  40

<210> SEQ ID NO 2
<211> LENGTH: 39
<212> TYPE: PRT
<213> ORGANISM: Stropharia rugosoannulata Farlow in Murr.
<220> FEATURE:
<221> NAME/KEY: MISC_FEATURE
<222> LOCATION: (4)..(4)
<223> OTHER INFORMATION: X stands for Pro/Gly.
<220> FEATURE:
<221> NAME/KEY: MISC_FEATURE
<222> LOCATION: (7)..(7)
```

```
<223> OTHER INFORMATION: X stands for Glu/Lys.
<220> FEATURE:
<221> NAME/KEY: MISC_FEATURE
<222> LOCATION: (9)..(9)
<223> OTHER INFORMATION: X stands for Val/Asp.
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (13)..(13)
<223> OTHER INFORMATION: X stands for Asn/Asp/Glu.
<220> FEATURE:
<221> NAME/KEY: MISC_FEATURE
<222> LOCATION: (17)..(17)
<223> OTHER INFORMATION: X stands for any amino acid, preferably Cys.
<220> FEATURE:
<221> NAME/KEY: MISC_FEATURE
<222> LOCATION: (20)..(20)
<223> OTHER INFORMATION: X stands for His/Ser.
<220> FEATURE:
<221> NAME/KEY: MISC_FEATURE
<222> LOCATION: (27)..(27)
<223> OTHER INFORMATION: X stands for Lys/His.
<220> FEATURE:
<221> NAME/KEY: MISC_FEATURE
<222> LOCATION: (29)..(29)
<223> OTHER INFORMATION: X stands for Val/Ile.
<220> FEATURE:
<221> NAME/KEY: MISC_FEATURE
<222> LOCATION: (33)..(33)
<223> OTHER INFORMATION: X stands for Gly/Asn/Ser.
<220> FEATURE:
<221> NAME/KEY: MISC_FEATURE
<222> LOCATION: (34)..(34)
<223> OTHER INFORMATION: X stands for Ala/Thr.
<220> FEATURE:
<221> NAME/KEY: MISC_FEATURE
<222> LOCATION: (39)..(39)
<223> OTHER INFORMATION: X stands for Arg/Thr.

<400> SEQUENCE: 2

Ala Pro Val Xaa Val Tyr Xaa Leu Xaa Xaa Asp Gly Xaa Ser Thr Lys
1               5                   10                  15

Xaa Thr Ala Xaa Leu Asp Tyr Gly Asp Gly Xaa Trp Xaa Ala Gln Trp
            20                  25                  30

Xaa Xaa Asn Val Phe His Xaa
        35

<210> SEQ ID NO 3
<211> LENGTH: 40
<212> TYPE: PRT
<213> ORGANISM: Lepista sordida (Schum. : Fr.) Sing.
<220> FEATURE:
<221> NAME/KEY: MISC_FEATURE
<222> LOCATION: (1)..(1)
<223> OTHER INFORMATION: X stands for Ala/Gln.
<220> FEATURE:
<221> NAME/KEY: MISC_FEATURE
<222> LOCATION: (4)..(4)
<223> OTHER INFORMATION: X stands for Pro/Lys.
<220> FEATURE:
<221> NAME/KEY: MISC_FEATURE
<222> LOCATION: (7)..(7)
<223> OTHER INFORMATION: X stands for Ala/Ser.
<220> FEATURE:
<221> NAME/KEY: MISC_FEATURE
<222> LOCATION: (8)..(8)
<223> OTHER INFORMATION: X stands for Met/Ile/Val.
<220> FEATURE:
<221> NAME/KEY: MISC_FEATURE
<222> LOCATION: (9)..(9)
<223> OTHER INFORMATION: X stands for Tyr/Thr.
<220> FEATURE:
```

```
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (13)..(13)
<223> OTHER INFORMATION: X stands for Asp/Asn.
<220> FEATURE:
<221> NAME/KEY: MISC_FEATURE
<222> LOCATION: (16)..(16)
<223> OTHER INFORMATION: X stands for Lys/Glu.
<220> FEATURE:
<221> NAME/KEY: MISC_FEATURE
<222> LOCATION: (17)..(17)
<223> OTHER INFORMATION: X stands for any amino acid, preferably Cys.
<220> FEATURE:
<221> NAME/KEY: MISC_FEATURE
<222> LOCATION: (20)..(20)
<223> OTHER INFORMATION: X stands for Ala/Asn.
<220> FEATURE:
<221> NAME/KEY: MISC_FEATURE
<222> LOCATION: (22)..(22)
<223> OTHER INFORMATION: X stands for Val/Asp/Asn.
<220> FEATURE:
<221> NAME/KEY: MISC_FEATURE
<222> LOCATION: (25)..(25)
<223> OTHER INFORMATION: X stands for Asp/Asn.
<220> FEATURE:
<221> NAME/KEY: MISC_FEATURE
<222> LOCATION: (27)..(27)
<223> OTHER INFORMATION: X stands for Arg/His/Asn.
<220> FEATURE:
<221> NAME/KEY: MISC_FEATURE
<222> LOCATION: (31)..(31)
<223> OTHER INFORMATION: X stands for Gln/Arg.
<220> FEATURE:
<221> NAME/KEY: MISC_FEATURE
<222> LOCATION: (34)..(34)
<223> OTHER INFORMATION: X stands for Thr/Val.

<400> SEQUENCE: 3

Xaa Pro Val Xaa Val Lys Xaa Xaa Xaa Xaa Asp Gly Xaa Thr Tyr Xaa
1               5                   10                  15

Xaa Thr Ala Xaa Leu Xaa Tyr Gly Xaa Gly Xaa Trp Val Ala Xaa Trp
            20                  25                  30

Ser Xaa Ala Val Phe His Gln Ser
        35                  40

<210> SEQ ID NO 4
<211> LENGTH: 27
<212> TYPE: PRT
<213> ORGANISM: Naematoloma sublateritium (Fr.) Karst/Hypholoma
      sublateritium(Fr.)Quel
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (13)..(13)
<223> OTHER INFORMATION: X stands for Asp/Thr.
<220> FEATURE:
<221> NAME/KEY: MISC_FEATURE
<222> LOCATION: (14)..(14)
<223> OTHER INFORMATION: X stands for Ser/Ala.
<220> FEATURE:
<221> NAME/KEY: MISC_FEATURE
<222> LOCATION: (16)..(16)
<223> OTHER INFORMATION: X stands for Gln/Lys.
<220> FEATURE:
<221> NAME/KEY: MISC_FEATURE
<222> LOCATION: (17)..(17)
<223> OTHER INFORMATION: X stands for any amino acid, preferably Cys.
```

```
<400> SEQUENCE: 4

Ala Pro Val Pro Val Thr Lys Leu Val Xaa Asp Gly Xaa Xaa Phe Xaa
1               5                   10                  15

Xaa Thr Ala Asn Leu Asp Phe Gly Asp Gly Asn
            20                  25

<210> SEQ ID NO 5
<211> LENGTH: 40
<212> TYPE: PRT
<213> ORGANISM: Naematoloma sublateritium (Fr.) Karst/Hypholoma
      sublateritium(Fr.)Quel
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (14)..(14)
<223> OTHER INFORMATION: X stands for Asp/Thr.
<220> FEATURE:
<221> NAME/KEY: MISC_FEATURE
<222> LOCATION: (15)..(15)
<223> OTHER INFORMATION: X stands for Ser/Ala.
<220> FEATURE:
<221> NAME/KEY: MISC_FEATURE
<222> LOCATION: (17)..(17)
<223> OTHER INFORMATION: X stands for Gln/Lys.
<220> FEATURE:
<221> NAME/KEY: MISC_FEATURE
<222> LOCATION: (18)..(18)
<223> OTHER INFORMATION: X stands for any amino acid, preferably Cys.

<400> SEQUENCE: 5

Ala Pro Val Pro Val Thr Lys Leu Val Xaa Asp Asp Gly Xaa Xaa Phe
1               5                   10                  15

Xaa Xaa Thr Ala Asn Leu Asp Phe Gly Asp Gly Asn Trp Val Ala Gln
            20                  25                  30

Trp Ser Thr Asn Val Phe His Asn
            35                  40
```